US008784380B2

United States Patent
Wall

(10) Patent No.: US 8,784,380 B2
(45) Date of Patent: *Jul. 22, 2014

(54) METHOD AND DEVICE FOR PAINLESS INJECTION OF MEDICATION

(75) Inventor: Eric James Wall, Cincinnati, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 386 days.

This patent is subject to a terminal disclaimer.

(21) Appl. No.: 12/630,996

(22) Filed: Dec. 4, 2009

(65) Prior Publication Data

US 2010/0076400 A1   Mar. 25, 2010

Related U.S. Application Data

(62) Division of application No. 10/605,187, filed on Sep. 12, 2003, now Pat. No. 7,637,891.

(60) Provisional application No. 60/410,130, filed on Sep. 12, 2002.

(51) Int. Cl.
  *A61M 5/20*    (2006.01)
  *A61M 5/32*    (2006.01)

(52) U.S. Cl.
  USPC .......................................... 604/135; 604/180

(58) Field of Classification Search
  USPC ........... 604/890.1, 891.1, 131–151, 156, 157, 604/892.1
  See application file for complete search history.

(56) References Cited

U.S. PATENT DOCUMENTS

| 4,324,237 | A  | * | 4/1982  | Buttaravoli ....................... 602/54 |
| 5,527,287 | A  | * | 6/1996  | Miskinyar ....................... 604/135 |
| 6,585,707 | B2 | * | 7/2003  | Cabiri et al. ..................... 604/307 |
| 6,749,587 | B2 | * | 6/2004  | Flaherty .......................... 604/151 |
| 7,252,653 | B2 | * | 8/2007  | Ueda et al. ...................... 604/272 |
| 7,637,891 | B2 | * | 12/2009 | Wall .............................. 604/131 |
| 7,670,314 | B2 | * | 3/2010  | Wall et al. ...................... 604/135 |
| 7,896,841 | B2 | * | 3/2011  | Wall et al. ...................... 604/135 |

* cited by examiner

*Primary Examiner* — Matthew F Desanto
(74) *Attorney, Agent, or Firm* — Faegre Baker Daniels LLP

(57) ABSTRACT

A method for providing a substantially painless injection of medication into a patient, including inserting an injection needle having an outside diameter greater than 0.20 mm and less than about 0.38 mm, and injecting a medicament through the needle and into the patient at a substantially constant volumetric flow rate of about 0.05 µL/s to about 50 µL/s that provides a painless injection. The method does not require the use of an anesthetic or that the medical personnel to spend a substantial amount of time performing the injection procedure, is relatively simple and inexpensive to perform and operate, and provides a relatively high degree of safety for both the medical personnel and for the patient.

15 Claims, 14 Drawing Sheets

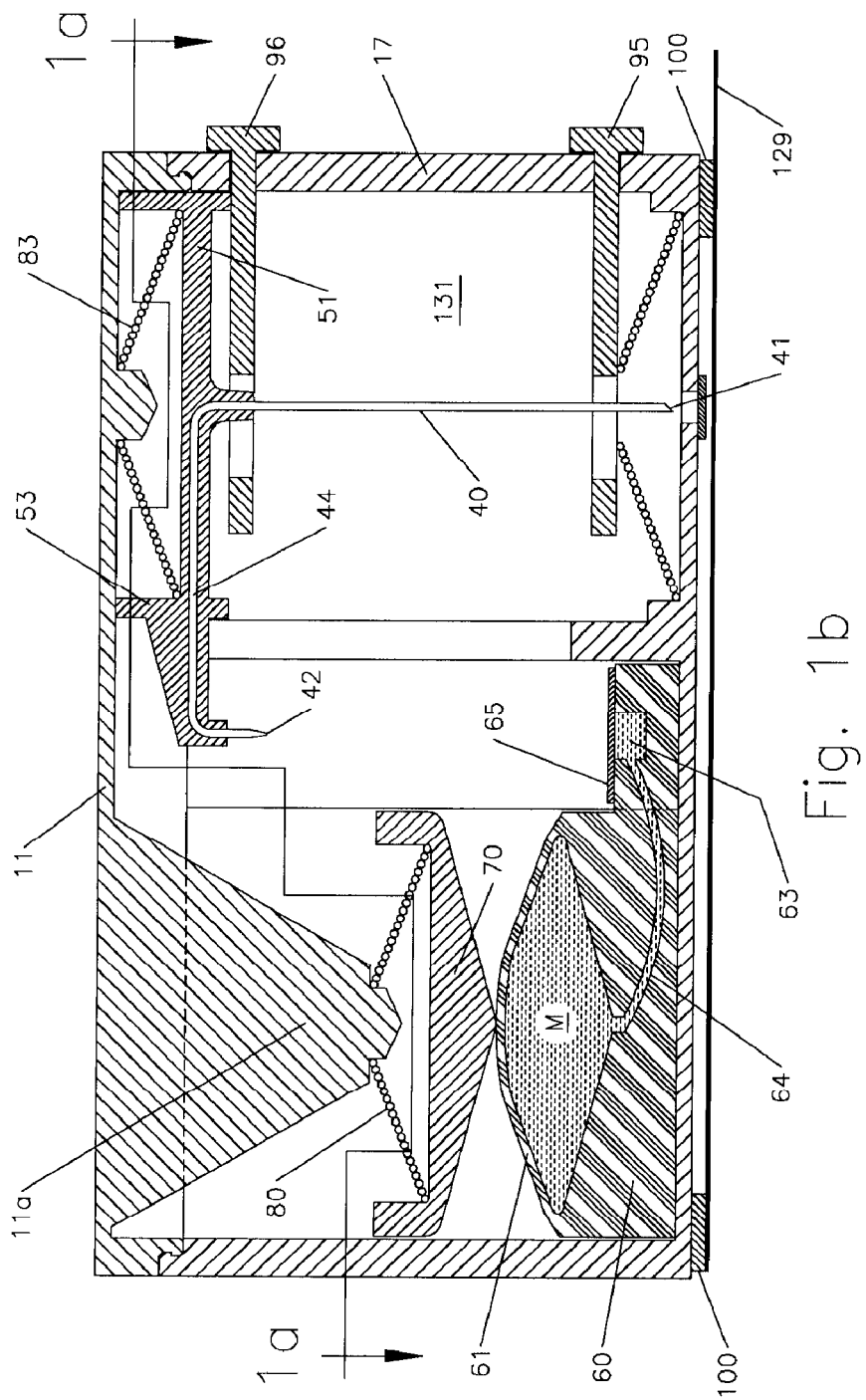

METHOD AND DEVICE FOR PAINLESS INJECTION OF MEDICATION

CROSS-REFERENCE TO RELATED APPLICATIONS

This application is a divisional application of U.S. application Ser. No. 10/605,187, filed Sep. 12, 2003 now U.S. Pat. No. 7,637,891, which claims the priority of U.S. Provisional Patent Application No. 60/410,130, filed Sep. 12, 2002, the disclosures of which are incorporated herein by reference.

BACKGROUND

The present invention relates to injecting medication and, more particularly, to a substantially painless method and a device for performing the method of injecting medication into a patient.

Conventional medical injection devices for injecting medication into the muscle or tissue of a patient typically comprise some form of a manual hypodermic syringe. Generally speaking, a hypodermic syringe consists of a cylindrical barrel having a chamber that provides a reservoir for a liquid medication, a distal end adapted to be connected to a hollow hypodermic needle and for placing one end of the needle into flow communication with the medication contained within the chamber, and a proximal end adapted for receiving a stopper and plunger assembly. The stopper and plunger assembly includes a stopper effective for moving along the barrel chamber and an elongated plunger effective for causing movement of the stopper. The needle of the hypodermic syringe is manually inserted into the patient through the skin. The stopper is moved along the barrel chamber by applying axial force to the plunger, thereby forcing the liquid medication out of the barrel chamber, through the hypodermic needle and into the muscle or tissue of the patient.

Receiving an injection by such a conventional device can be a very traumatic experience, particularly for a child. The child's fears and that of the child's parent, can become a significant medical problem if it leads to the child not receiving a required vaccination. These fears are predominately caused by pain which is associated with injections given by conventional injection devices and methods.

Studies have shown that the pain associated with an injection is related to the size of the needle and the flow rate at which the medication is injected. It has been found that the amount of pain or discomfort experienced by a patient increases as the outside diameter of the needle increases. It has also been found that high flow rates of medication injection (e.g., about 0.5-2 ml per second) into the patient can tear internal tissue and cause pain. The tearing of tissue is caused by the build-up of excessive pressure within the tissue when the surrounding tissue is unable to quickly absorb the injected medication.

While the injection of a medication at a relatively slow flow rate is more comfortable for the patient, the increased amount of time the syringe remains in the hand of the medical personnel can make the technique tiring for such personnel as well as the patient. In addition, small vibrations or disturbances of the needle caused by movement of the medical personnel or the patient can result in pain to the patient. It is known that the fluctuation of flow rate of the injection of medication being delivered by a hand-held syringe can vary greatly. It is extremely difficult, if not impossible, to deliver an steady, very slow flow of medication from a hand-operated syringe (the human thumb depressing the syringe plunger) over an extended amount of time.

It has also been found that the sight of the hypodermic needle by itself is often enough to cause many patients to become anxious and tense. This reaction in turn may cause the patient's muscles to become tight and hard, making needle penetration even more difficult and painful.

A number of methods and devices have been developed for reducing or eliminating the pain and discomfort associated with medical injections. One such method includes the application of a topical anesthetic to the injection site on the patient's skin prior to the injection, which itself can be painful. While this method has reduced some of the discomfort associated with injections, the topical anesthetic does not substantially penetrate the skin into the deeper skin and muscle tissue. Substantial pain and discomfort with intramuscular injections can remain.

Another technique for reducing the pain and discomfort associated with medical injections includes the step of injecting an anesthetic at the site of the injection using a fine gauge needle, then inserting the larger medication hypodermic needle through the anesthetized skin to inject the medication at a constant and slow flow rate intramuscularly at the desired depth. Unfortunately, injecting an anesthetic into a patient is not always desirable and the technique is relatively expensive and impractical for many routine injection procedures.

In addition to reducing pain or discomfort to the patient, safety has also become a principal concern to medical personnel. Special precautions must be taken to avoid accidental needle sticks that could place a user at serious risk because of the danger from fluid borne pathogens. Despite the taking of special precautions, there still remains the possibility of an accidental needle contact and attendant injury. Accordingly, medical injection devices should operate to minimize the possibility of injury caused by accidental needle sticks.

In recent years, increased emphasis has been placed on establishing treatment protocols aimed at providing a patient as well as medical personnel with greater freedom of movement. To this end, there is a great deal of interest in the development of light weight and easy-to-use portable injection devices.

Accordingly, a need exists for substantially painless method and an apparatus for performing the method of injecting medication into a patient that does not require the use of an anesthetic, that does not require the medical personnel to spend a substantial amount of time performing a particular procedure, that is relatively simple, portable and inexpensive to perform and operate, that permits the patient a relatively high degree of movement during the injection, and that provides a relatively high degree of safety for both the medical personnel and for the patient.

SUMMARY OF INVENTION

The present invention relates to devices for painlessly injecting medications, and a method for providing a substantially painless injection of medication into a patient that does not require the use of an anesthetic, that does not require the medical personnel to spend a substantial amount of time performing the injection procedure, that is relatively simple and inexpensive to perform and operate, and that provides a relatively high degree of safety for both the medical personnel and for the patient.

The present invention relates to a self-contained device for painless, inter-muscular injection of a liquid medicament, comprising: a) a housing having a base for attachment to the skin of a patient, b) an injection needle disposed substantially perpendicular to the base and within the housing, the needle having an injection end, and configured for axial movement between a first position wherein the injection end is within the housing and a second position wherein the injection end extends outwardly from the base to a distance sufficient for intramuscular insertion thereof, the injection needle having an outside diameter greater than 0.20 mm and less than about 0.38 mm, c) a reservoir containing a liquid medicament, d) a means for liquid communication between the reservoir and the injection needle, e) a means for inserting the injection needle to its second position, and f) a means for pumping the medicament from the reservoir to the injection end of the needle.

The present invention relates to a self-contained device for painless, inter-muscular injection of a liquid medicament, comprising: a) a housing having a base for attachment to the skin of a patient, b) an injection needle disposed substantially perpendicular to the base and within the housing, the needle having an outside diameter less than about 0.38 mm, an inlet end and an opposed injection end, and configured for axial movement between a first position wherein the injection end is within the housing and a second position wherein the injection end extends outwardly from the base to a distance sufficient for intramuscular insertion thereof, c) a reservoir containing a liquid medicament, disposed within the housing along a line extending axially from the inlet end of the injection needle, d) a means for inserting the injection needle to its second position, and e) a reservoir urging means for moving the reservoir into liquid communication with the inlet end of the injection needle.

The present invention additionally relates to a self-contained device for painless, inter-muscular injection of a liquid medicament, comprising: a) a housing having a base for attachment to the skin of a patient, b) an injection needle disposed substantially perpendicular to the base and within the housing, the needle having an outside diameter less than about 0.38 mm, inlet end and an opposed injection end, and being configured for axial movement between a first position wherein the injection end is within the housing and a second position wherein the injection end extends outwardly from the base, a reservoir containing a liquid medicament, d) a means for liquid communication between the reservoir and the injection needle, e) a means for inserting the injection needle to its second position, f) a means for pumping the medicament from the reservoir to the injection end of the injection needle at a substantially constant volumetric flow rate of from about 0.5 µL/s to about 20 µL/s.

The present invention also relates to a self-contained device for painless, inter-muscular injection of a liquid medicament, comprising: a) a housing having a base for attachment to the skin of a patient, b) an injection needle disposed within the housing, the needle having an outside diameter greater than 0.20 mm and less than about 0.32 mm, having an inlet end and an opposed injection end, and being configured for movement between a first position wherein the injection end is within the housing and a second position wherein the injection end extends through the base, c) a reservoir containing a liquid medicament, d) a means for liquid communication between the reservoir and the injection needle, e) a means for inserting the injection needle to its second position, f) a means for pumping the medicament from the reservoir to the injection end of the injection needle at a substantially constant volumetric flow rate of from about 0.5 µL/s to about 20 µL/s.

The present invention can also relate to a self-contained device for painless, inter-muscular injection of a liquid medicament, comprising: a) a housing having a base for attachment to the skin of a patient, b) an injection needle disposed substantially perpendicular to the base and within the housing, the needle having an outside diameter less than about 0.038 mm, inlet end and an opposed injection end, and being configured for axial movement between a first position wherein the injection end is within the housing and a second position wherein the injection end extends outwardly from the base, c) a reservoir containing a liquid medicament, d) a means for liquid communication between the reservoir and the injection needle, e) a means for inserting the injection needle to its second position, f) a means for pumping the medicament from the reservoir to the injection end of the injection needle at a substantially constant volumetric flow rate of from about 0.5 µL/s to about 20 µL/s.

The present invention relates to a self-contained device for painless injection of a liquid medicament, comprising: a) a housing having a base for attachment to the skin of a patient, b) an injection needle disposed substantially perpendicular to the base and within the housing, the needle having an injection end, and configured for axial movement between a first position wherein the injection end is within the housing and a second position wherein the injection end extends outwardly from the base, the injection needle having an outside diameter greater than 0.20 mm and less than about 0.38 mm, c) a reservoir containing a liquid medicament, d) a means for liquid communication between the reservoir and the injection needle, e) a means for pre-selecting the depth of extension of the injection needle at its second position, f) a means for inserting the injection needle to its second position, and g) a means for pumping the medicament from the reservoir to the injection end of the needle.

The present invention relates further to a self-contained, automatically-sequencing device for painless, inter-muscular injection of a liquid medicament, comprising: a) a housing having a base for attachment to the skin of a patient, b) an injection needle disposed within the housing, the needle having an outside diameter less than about 0.38 mm, an inlet end and an opposed injection end, and being configured for movement between a first position wherein the injection end is within the housing and a second position wherein the injection end extends the base, c) a reservoir containing a liquid medicament, d) a means for liquid communication between the reservoir and the injection needle, e) a means for inserting the injection needle to its second position, f) a means for pumping the medicament from the reservoir to the injection end of the needle, g) a means for retracting the injection needle from its second position to a third position within the housing, and h) a means for automatically sequencing and activating the inserting means, the pumping means and the retracting means.

The present invention also can relate to a self-contained device for injecting a medicament, comprising: a) a housing having a base for attachment to the skin of a patient, b) an injection needle disposed within the housing and having an injection end configured for insertion into the skin of the patient, c) a reservoir containing a liquid medicament and configured for liquid communication with the injection needle, d) a bandage releasably affixed to the base of the housing, comprising a base-contacting surface and a skin-contacting surface that comprises an affixment for attachment of the device to the skin.

The present invention relates further to a method of administering a liquid medicament in an inter-muscular injection painlessly to a patient, comprising the steps of: a) inserting the injection tip of an injection needle through the skin and into the muscle of a patient, the needle having an outside diameter greater than 0.20 mm and less than about 0.38 mm, and b) injecting the liquid medicament through the needle and into the patient at a substantially constant volumetric flow rate of from about 0.5 µL/s to about 20 µL/s.

BRIEF DESCRIPTION OF FIGURES

FIG. 1b shows a cross sectional view of the painless injection device of the present invention, taken along section line 1b-1b of FIG. 1a.

FIG. 2g shows a plan view of the painless injection device of FIG. 1a, viewed from line 2g-2g of FIG. 2a.

FIG. 4b shows a cross sectional view of the painless injection device of FIG. 4a.

DETAILED DESCRIPTION OF INVENTION

Figure 1A:
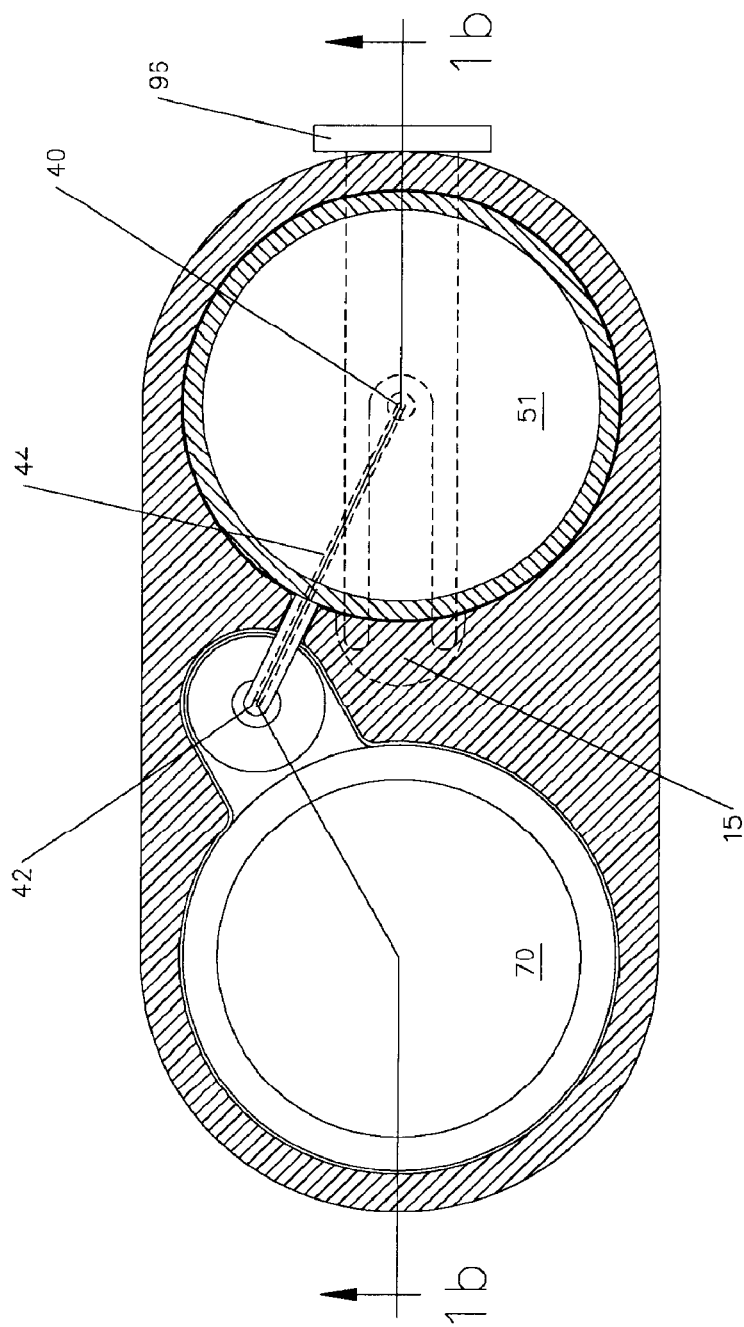
FIG. 1a shows a cross sectional view of a painless injection device of the present invention, taken along section line 1a-1a of FIG. 1b.

Typically, the devices are self-contained devices for injecting the medication into a patient. The self-contained device typically embodies a housing and a plurality of elements associated with and at least semi-permanently attached to the housing. The other elements include an injection needle and a reservoir for containing a supply of the medicament. The other associated elements can also include the various means of powering the functional operations of the devices, such as the insertion and retraction of the injection needle, and the pumping of medicament to the injection needle.

Typically, these associated elements are contained within the confines of the housing, although these elements can also partially confront or penetrate through the outer surface of the housing.

In the course of administering most injections of vaccines and other medicaments, the injection can be advantageously administered intramuscularly, that is, into the muscle. The injection is by an injection needle that is configured for insertion through the outer surface of the subject's skin, and through the skin, and more typically into the muscle tissue of the subject. Typically, the depth of insertion is at least about 5 mm, and typically up to about 35 mm or more, more typically from about 12 mm to about 25 mm, and even more typically from about 22 mm to about 26 mm. For a young child or infant, the depth of insertion is typically from about 10 mm to about 25 mm, more typically from about 15 mm to about 20 mm. Alternatively, some injections can be administered intradermally, or into other internal organs or the general body cavity of the subject.

The self-contained devices of the invention are intended to be attached semi-permanently to the skin of the subject. The devices are typically configured to be attached to the upper arm or to the thigh area, providing access to the larger skeletal muscles (the deltoids and the quadriceps) for intramuscular injection. The attachment is preferably semi-permanent, whereby the device can be removed reasonably easily after attachment to the skin, and the device does not move or migrate along the surface of the skin after attachment. In many situations, an adequate adhesive attachment is sufficient. Alternative attachment means can include strapping, such as with a buckle strap or with a "hook and loop" attachment means commonly referred to as "Velcro", or cuffing, as with a sphygmomanometer cuff.

A typical adhesive for securing the device directly to the skin is a pressure sensitive adhesive (PSA). The direct-attaching PSA and the base where the PSA is affixed are typically configured whereby the PSA has an adhesive affixment to the device greater than the adhesive affixment to the skin. The PSA is typically configured for permanent affixment to the device. The PSA is also selected for a secure though releasable affixment to the skin. These criteria ensure that the device can be securely affixed to the skin for the injection procedure, and can be safely and efficiently removed from the skin thereafter.

An embodiment of the device can comprise an adhesive attachment means, typically a pressure sensitive adhesive 100. Typically, the device having a direct-attaching PSA will also include a release member, such as a release paper or film, that overlies the adhesive on its skin-contacting side. The release member is peeled from the PSA prior to attachment to the skin. After removal of the release paper, the exposed adhesive layer can be placed against the patient's skin to attach the device thereto.

A main objective for initiating the development of the present injection was effecting a painless injection of vaccines and other medicaments. While pain can be a relative experience, typically the painless device of the present invention will, after having been secured to the skin of the patient, effect the insertion of the injection needle and injection of the medicament into the body without any sensation or feeling of pain, and more typically without any sensation or feeling whatsoever. In other words, the patient is most situations will have no sensation that the device has inserted a needle into the body, or that medicament is or has been injected into the body, except perhaps visually observing the device or touching the device with a hand, or feeling the attachment of the device to the outside of the skin.

Typically the device is configures to inject the medication into the subject without the power or control of either the patient or other person to effect the injection. The device and method of the invention enables injection of vaccines and other medicaments without requiring medical personnel to inject or hold the device. The use of the device for injection allows medical personnel to perform other tasks while the injection is being administered. The device also allows the patient to have freedom of movement for the minutes of time that the injection is being administered.

Typically, the device is intended to be self-powered, wherein the device comprises a power means to provide the energy necessary for one or more of the functions of the device, such as inserting the injection needle, pumping the medicament to the injection needle, and withdrawing the injection needle from the skin. The power means can include one or more such power means, each of which can employ one or more different forms of power. Typically, the power means include electrical power, supplied from a battery or electrical condenser. The power means can also include a pneumatic power means, such as a source of compressed gas or air. The power means can also include a fluidic power means, which includes both pneumatic and hydraulic power, such as a source of compressed air or gas, or hydraulic fluid. The power means can also include a mechanical power means, such as a compressed, stretched or torsioned spring, or a physical member that is biased into a strained or stressed position. The power means can also include a chemical power means, an electronic power means, such as an energized piezoelectric material, or an electrical power means such as an energized coil. The power means can also include an electro-chemical power means, where an electric charge or current can be converted into a chemical source of power, such as gas pressure from a gas generator.

The device is also at least partially self-controlled, wherein at least one of the elements of the device can function automatically in response to the operation of another element. In some embodiments, all of the functioning elements of the device are actuating in response to the operation of one other element, or in response to some outside parameter, or automatically by time.

The power means can be used to provide energy to one or more of the elements of the device, such as insertion and retraction of the injection needle, or pumping of the medicament. Alternative power means can be used to provide energy for different elements, wherein the injection needle if moved from one position to another by a first power means, and a liquid medicament is pumped from a reservoir to the injection needle by a different, second power means.

The typical device of the present invention has a housing. The housing comprises a base for placement against the skin of a patient for attachment. Typically, the base has a contoured surface that generally conforms to the shape of the body or skin, to maintain the base surface in optimum confronting relationship with the skin. In a typical embodiment for use with intramuscular injections, the base of the device has a slightly concave surface, which arches inwardly toward the interior of the housing.

The housing is typically made of a thermoplastic material that is light, inexpensively manufactured such as by molding, yet durable and resilient to gross deformation. Typical plastic materials can include polyethylene or polypropylene. The housing can be designed with a shape that is both aesthetically pleasing and functional to house the injection needle, reservoir, and other elements of the device.

The housing also provides a visual enclosure for the injection needle that keeps the needle out of sight of the patient at all times during the injection procedure. This reduces or eliminates the patient's apprehension or fear caused by the sight of a hypodermic needle, thereby reducing the tendency of the patient's muscles to tighten and harden, which can make needle penetration more difficult and painful.

The housing also provides a physical enclosure for the injection needle that helps to avoid accidental needle sticks that could place a user at serious risk from fluid-borne pathogens. The device can be configured for use only once (unless completely disassembled and retrofitted), thereby minimizing the likelihood of reuse of a contaminated hypodermic needle.

The injection needle of the device provides for liquid communication of the medicament passing from the reservoir of the device into the body tissue of the patient, from where the medicament can dissipate into the surrounding tissue and throughout the body. The injection needle should be shaped and configured to provide painless insertion and painless injection of the medicament. Generally an injection needle having a smooth circular outer surface and an outer diameter D of about 0.36 mm (28 gauge needle) and less can be inserted painlessly through the skin of a patient. For small children, infants and patients having more sensitive skin, an outer diameter D of about 0.30 mm (30 gauge needle) and less (31 gauge to 33 gauge), will typically ensure painless needle insertion.

Typically the injection needle is configured to be substantially linear or straight, from its tip toward the opposed inlet opening. The needle can be configured to be linear to its inlet end, or can be configured having a bent or curved portion near the inlet opening.

The needle size should be sufficiently large to allow passage of the required volume of liquid medicament into the body within a period of time that is suitable to avoid causing pain. For a typical medicament volume of about 0.5 ml to about 1.0 ml, a substantially painless to completely painless injection can be achieved over an injection period of from about 1 minute to about 10 minutes, more typically from about 3 minutes to about 5 minutes. The volumetric flow rate is at least about 0.05 microliter per second µL/s, and up to about 50 µL/s. Typically, the volumetric flow rate is about 0.5 µL/s to about 20 µL/s, and more typically about 1 µL/s to about 4 µL/s. The injection needle should be sufficiently durable and axially rigid to avoid bending or breaking when inserted into the skin and muscle. Typically, a needle having an outer diameter of from 0.20 mm (33 gauge), more typically of from 0.23 mm (32 gauge), to 0.36 mm (28 gauge), is sufficiently painless, durable, and liquid conductive.

The medicament is typically contained within the cavity of a reservoir, and flows from the reservoir to the injection needle during injection. The reservoir is typically positioned within the housing, as shown in the illustrated embodiment, though the structure of the reservoir can also form a portion of the outer surface of the housing. The reservoir can have a rigid structure where its volume is fixed. The reservoir more typically has a flexible structure where its volume can decrease as its contents of medicament is removed there from. Typical materials for use in making the reservoir include natural and synthetic rubber, polyolefin, and other elastomeric plastics. The selection of the structure and material of construction of the reservoir will depend in part on the specific means of pumping the medicament from the reservoir to the injection needle, as discussed herein after. A reservoir will generally have a volume sufficient to contain about 0.1 ml to about 3 ml of medicament. In a typical embodiment, the reservoir would hold about 0.5 ml to about 1.0 ml of medicament.

A typical embodiment of a reservoir comprises a reservoir body having a cavity that has been pre-filled with a medicament and sealed, for assembly into the device. Selection of the material of the reservoir should also be chemically stable with the medicament.

Alternatively, a device comprising an empty reservoir can be filled by medical personnel with the appropriate quantity and type of medicament, prior to injection. Typically, the reservoir comprises a medication flow valve that has a self-closing, self-sealing opening to the cavity of the reservoir. The medication flow valve is typically an elastomeric or rubber material. The opening is typically a cylindrical member having a slit opening formed axially therethrough. The medication flow value can be inserted into a bore formed in the sidewall of the reservoir that is slightly smaller diameter than the flow valve. A hypodermic needle of a syringe can be inserted through the slit opening to inject a dose of liquid medication into the cavity of the reservoir. When withdrawn, the slit opening closes and seals itself.

Since a device is typically used by medical personnel as supplied, with the reservoir securely inserted within the housing, the device can have a companion flow valve disposed in the surface of the housing, or otherwise accessible to the medial personnel. If the reservoir is configured so that a portion of the reservoir is integral with the housing, then a single flow valve can be used, with an inlet accessible to the medical technician and an outlet into the cavity of the reservoir. Alternatively, the device can be configured with a second medication flow valve positioned in the housing, disposed adjacent to and aligned with the first flow valve disposed in the reservoir.

An important requirement of the liquid communication means is to ensure that the liquid medicament can flow from the reservoir to the injection needle regardless of the specific orientation of the device. Typically, the attachment of the device to the skin of the patient can position the reservoir and the injection needle into a variety of relative spatial orientations that can sometimes require the liquid medicament to flow upward against gravity, or that can position the outlet of the reservoir in an upward position, opposite the pool of medicament disposed in the reservoir.

Consequently, a preferred configuration of the reservoir and liquid communication means provides that the outlet of the reservoir is maintained in communication with the remaining liquid medicament in the reservoir. A typical configuration comprises a collapsible reservoir comprising an outlet that maintains liquid communication with any residual liquid medicament present in the reservoir. This reservoir has an upper flexible wall that can be conformed to the volume of the liquid remaining therein. The reservoir typically contains little or no air or gas when filled with the supply of liquid medicament and during the medicament displacement and injection operation. Thus, the reservoir collapses to become essentially empty, terminating medicament delivery. In like manner, when a non-flexible material is used for a reservoir such as a tube with plunger, as in a conventional hypodermic syringe, the displacement of the plunger empties the reservoir terminating delivery.

The housing can also comprise an outer support structure that confines and protects the reservoir from outside elements that might puncture it, and which can define the initial shape of the reservoir.

The reservoir can also be constructed of an elastomeric material that can be expanded in volume when fill with the liquid medicament supply, and holds medicament under pressure. After punctured by the inlet end of the injection needle, the expanded reservoir can contract to reduce the effective volume of the reservoir as liquid medicament is pumped there from. One or more of the walls of the reservoir can be made of an elastomeric material, while other walls or surfaces are made of other rubber or plastic material.

For pumping or dispensing the liquid medication from the cavity of the reservoir, a wall of the reservoir can be adapted to allow penetration thereof by a piercing conduit, such as the inlet end of a needle. Alternatively, a separate penetrable membrane can be affixed over an opening in a wall of the reservoir to provide a self-sealing, leak-proof joint when pierced by the piercing conduit.

The reservoir can also comprise an adaptable structure having a means of varying its effective volume, such as a piston-plunger construction or an accordion construction, as in a bellows. In the embodiments described herein, a self-contained reservoir can be replaced with a more conventional syringe and plunger for storing and injecting the medicament to the injection needle.

Non-limiting examples of a reservoir of the present invention are those described in U.S. Pat. No. 5,527,288 (element 10), U.S. Pat. No. 5,704,520 (element 12), and U.S. Pat. No. 5,858,001 (elements 16 and 17), all such publications incorporated herein by reference.

A first embodiment, of the present invention provides a self-contained device for painless, inter-muscular injection of a liquid medicament, comprising a housing, an injection needle, a reservoir containing a liquid medicament, a means for liquid communication between the reservoir and the injection needle, a first means for inserting the injection needle, and a means for pumping the medication from the reservoir to an injection end of the needle.

More specifically, the first embodiment provides a self-contained device for painless, inter-muscular injection of a liquid medicament, comprising: a) a housing having a base for attachment to the skin of a patient, b) an injection needle disposed substantially perpendicular to the base and within the housing, the needle having an injection end, and configured for axial movement between a first position wherein the injection end is within the housing and a second position wherein the injection end extends outwardly from the base to a distance sufficient for intramuscular insertion thereof, the injection needle having an outside diameter greater than about 0.20 mm and less than about 0.38 mm, c) a reservoir containing a liquid medicament, d) a means for liquid communication between the reservoir and the injection needle, e) a means for inserting the injection needle to its second position, and a means for pumping the medicament from the reservoir to the injection end of the needle.

An illustration of the first embodiment is shown in FIGS. 1*a*-1*d*. FIG. 1*b* shows the device 1 prior at attachment to the skin of a patient. FIG. 1*a* is a sectional view of the device shown in FIG. 1*b*, and FIG. 1*b* is a sectional view of the device shown in FIG. 1*a*. The device 1 comprises a housing 10, an injection needle 40, a medicament reservoir 60, a spring means 83 for inserting the needle, a spring means 86 for retracting the needle, and a means for establishing liquid communication between the reservoir and the needle, to pump liquid medicament to the injection needle.

The housing 10 has a base 12 having an opening 13 through which the injection needle 40 can extend, as described herein after. The opening 13 can be an opening in the base 12 surface that is sufficiently larger to accommodate the passing of the injection end 41 of the needle therethrough. The opening 13 can also have a penetrable covering 16 through which the injection needle can penetrate, such as a fabric or plastic film layer. The opening can also have a moveable cover or door (not shown) that is configured to move away from the opening, or to be moved away from the opening, by the passing of the injection needle 40 through the opening.

In the illustrated embodiment of FIG. 1*b*, the needle 40 has a U-shaped portion 44 at its inlet end. This allows the needle to be placed within the housing with its inlet end 42 oriented away from the top 11 of the housing to allow subsequent engagement of the inlet opening 42 to the reservoir 60.

In the first embodiment, the injection needle 40 is initially disposed in a first, stored position, substantially perpendicular to the base 12, and completely within the housing 10. For an intramuscular injection, the entry and passage of the injection needle through the skin is typically normal to the skin surface, although in an alternative embodiment, the needle can be inserted on an angle. The injection needle 40 has an injection end 41 and an inlet opening 42 end. The injection needle has an axial centerline (not shown) passing through the center of the interior passageway of the needle. The injection needle is typically linear from its tip towards the inlet end, at least for a distance sufficient for insertion along a linear insertion path. The injection needle is configured within the housing 10 to provide for axial movement along the centerline and extension outward from the base 12, between a first position wherein the injection end is within the housing, and a second position wherein the injection end extends to a distance sufficient for intramuscular insertion.

In its first or stored position, the tip 41 of the injection needle 40 is typically disposed inside the housing, sufficiently inboard from an opening to avoid an accidental sticking by the tip of the finger or skin of a patient or a person administering the injection. The inboard distance is typically about 1 mm or more. The tip 41 of the needle is extended in its second position to a distance sufficient for intramuscular insertion into the patient. The depth of insertion is the distance from the surface of the skin where the needle is inserted, to the tip of the injection needle when fully inserted into the body. In an embodiment having a means of adjusting the depth of insertion, discussed herein later, it is expected that medical technicians and physicians will adequately judge the appropriate depth of insertion of a specific patient, and adjust the device accordingly.

In the illustrated embodiment, the base 12 of the device surrounding the opening confronts and contacts the skin. In an embodiment where the base of the device is sufficiently concave whereby the base contacts the skin along a peripheral portion of the base, the opening can be positioned a distance offset and away from the skin surface. The movement of the injection needle from its first position to its second position involves its axial movement a distance equal to the sum of any inboard distance, any offset distance, and the insertion depth.

A means for liquid communication is provided between the reservoir 60 and the inlet opening 42 of the injection needle 40. A typical means for liquid communication comprises a passageway, illustrated by a reservoir inlet port 63. Reservoir inlet port 63 is formed in the body of the reservoir 60 and communicates via a first passage 64 to the cavity 63 of the reservoir. A penetrable membrane 65 covers the opening 67 to inlet port 63. The means for liquid communication also comprises the inlet opening 41 of the needle, and a mechanism, described later, for bringing the inlet end 41 into liquid communication with the inlet port 63.

The embodiment shown in FIGS. 1*a* and 1*b* disposes the reservoir 60 within the housing 10 and outside the pathway of an axial line extending along injection needle 40. This arrangement allows the height of the housing 12, from base 12 to the top 11, to be minimized, to just slightly more than the longitudinal length of the needle 40.

The insertion of the injection needle 40 into the skin and muscle of the patient can be achieved by an inserting means. Typically, the inserting means inserts the tip 41 of the needle rapidly into the tissue. A variety of means can be used as the inserting means. In the illustrated embodiment, a mechanical inserting means, such as a biasing member, shown as a spring 83, can be employed for inserting the needle. In FIG. 1*b*, the insertion spring 83 is shown positioned in compression between an insertion drive plate 51 and a top 11 of the housing. The insertion driving plate 51 has secured therethrough the injection needle 40, and is configured for movement normal to the base 12 and along the axial length of the insertion needle through a cavity 131. A first prong-shaped securing pin 96 removably penetrates the outer sidewall 17 and an inner wall 15 of the housing to secure the insertion driving plate 51, thereby retaining the injection needle, insertion driving plate 51, and the insertion spring 83 in an initial, stored position.

Prior to use the device 1, a release paper 129 covers portions of adhesive 100 disposed on the base 12 of the housing 10, as shown in FIG. 1*b*. To use the device, the release paper is removed and the device is adhered to the skin of a patient at the site of injection, as shown in FIG. 1*c*.

Figure 1C:
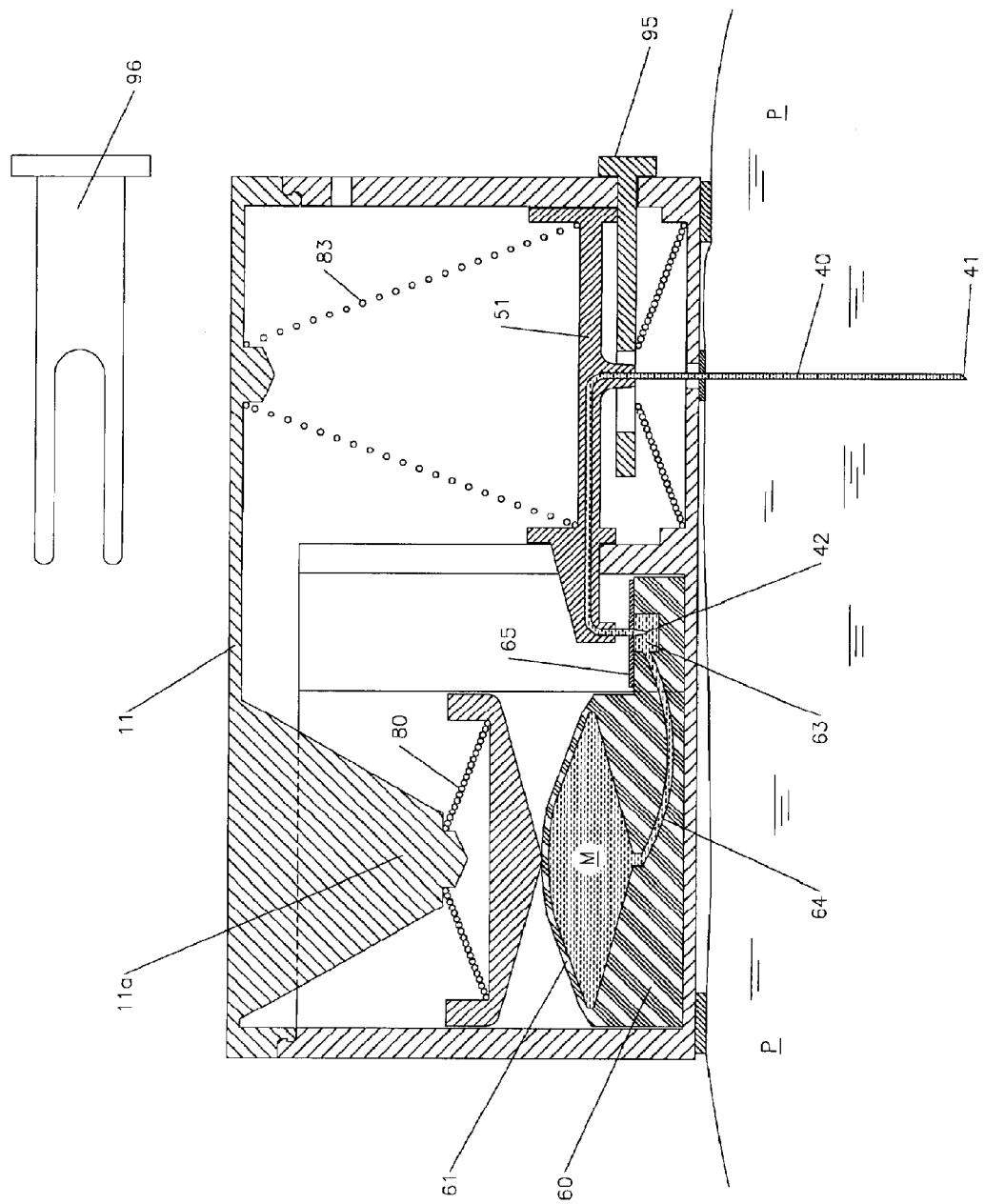
FIG. 1c shows a cross sectional view of the painless injection device of FIG. 1b, showing liquid medicament injection through an inserted needle.

When pin 96 is removed, as shown in FIG. 1*c*, the insertion spring 83 drives the insertion driving plate 51 downward along the axis of the insertion needle until stopped by an insertion stop, which in the illustrated embodiment is shown by element 95 (discussed hereinafter). During its travel, the insertion driving plate 51 thrusts the injection needle 40 into the tissue of the patient. Near the end of the thrust, the inlet opening 42 end of the injection needle is thrust into and penetrates through a first or upper side of the penetrable membrane 65 that is disposed over the opening of reservoir inlet port 63. When the inlet opening 42 penetrates through the penetrable membrane 65, it is placed into liquid communication with the reservoir 60 via passage 64. The penetrable membrane 65 is adapted to prevent any leakage of the liquid medicament along the outer surface of the inlet opening 42 end.

The device also comprises a means for pumping the medicament from the reservoir 60 to the injection tip 41 of the needle. In the illustrated embodiment, the pumping means comprises a mechanical pumping means, illustrated as a compression spring 80. The compression spring 80 is secured at a first end to a projection 11*a* integral with and extending from top 11, and exerts at its other end a substantially constant force F against the unsecured wall 61 of the reservoir 60, to place and maintain the medicament M in the reservoir 60 under pressure, whereby the medicament can flow from the reservoir 60 to the tip 41 of the injection needle. Proper selection of the reservoir material and the compression spring 80 can ensure a substantially constant liquid flow rate of the medicament through the injection needle, throughout the term of the medicament injection procedure. Alternatively, a flow restrictor can be placed anywhere in the line of fluid flow to help regulate the flow of medicament and its delivery rate to the patient.

Figure 1D:
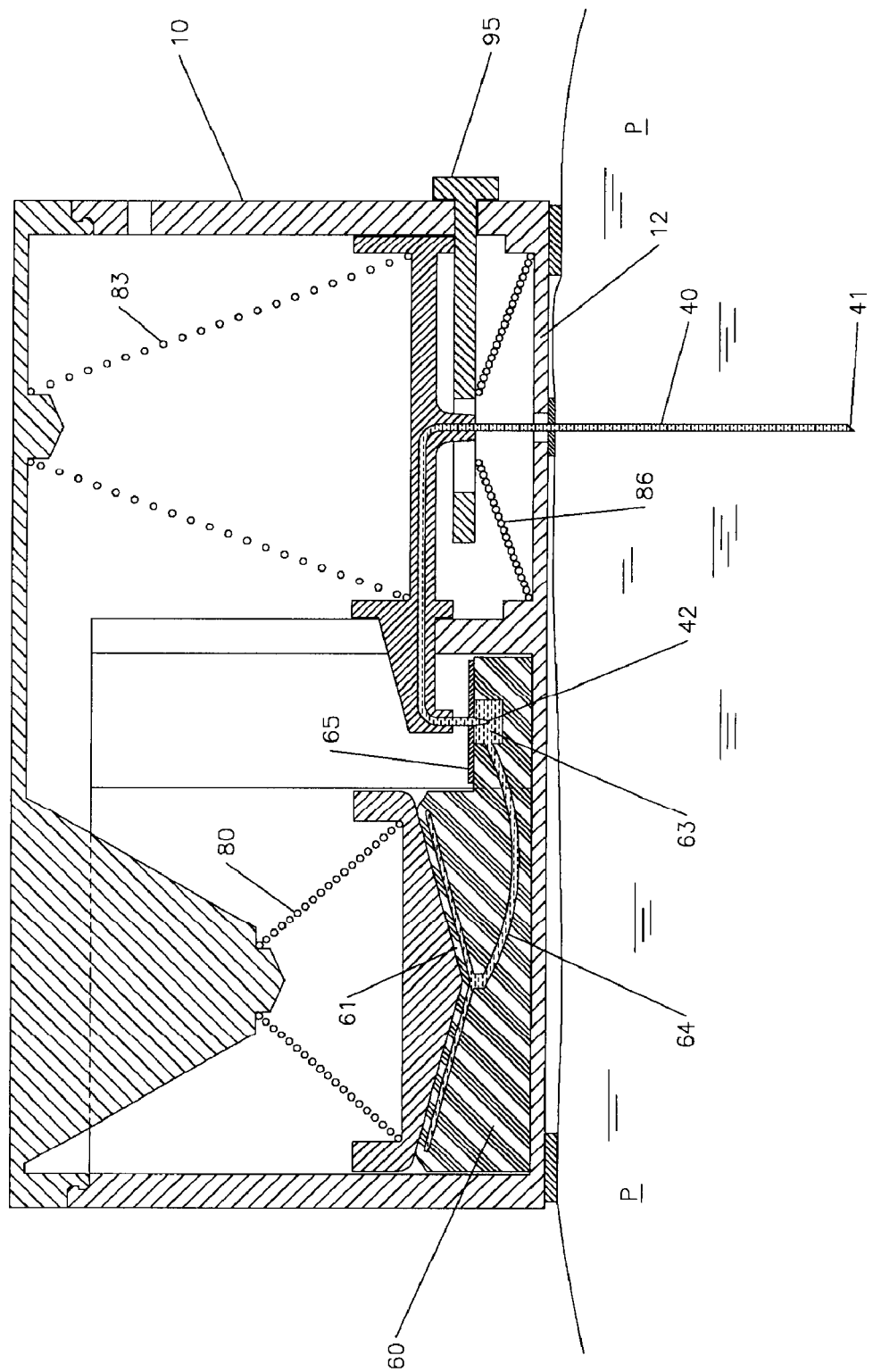
FIG. 1d shows a cross sectional view of the painless injection device of FIG. 1b, showing completion of the liquid medicament injection.

The reservoir 60 is typically configured where the outer wall 61 will collapse inwardly against the opposed inner wall, as shown in FIG. 1*d*, until the reservoir is essentially empty.

At a predetermined time, or when it is determined that the medicament has been substantially completely injected into the patient, the injection needle can be withdrawn from the patient's tissue. The device with the injection needle extending therefrom can then be pulled from the skin by hand. There are, however, advantages for retracting the injection needle back into a third position within the housing, prior to removal of the device from the patient. First, there is always a concern for and the possibility that the act of manually removing the inserted needle can cause pain or injury to the patient, especially when the needle has been inserted intramuscularly, or when the patient is non-cooperative during needle withdrawal. An infant or a small child, for example, may struggle or find it difficult to sit still and calmly while the needle is manually withdrawn. Second, manual removal of the device while the needle is extended raises a significant potential for an unintended needle stick from the exposed extended needle. Third, the sight of the exposed needle can cause anxiety in a patient.

Consequently, an optional element of a typical embodiment of the invention will comprises a retracting means for retracting the injection needle between its second position and a third position within the housing. Typically, the retracting means withdraws the needle with its tip 41 rapidly from the tissue and back into the housing 10. A variety of means can be used as the retracting means. In the illustrated embodiment in FIGS. 1*d* and 1*e*, a mechanical retracting means such as a biasing member, shown as a spring 86, can be employed for retracting the needle. The retraction spring 86 is shown positioned in compression between a second prong-shaped securing pin 95 and the base 12 of the housing. The second securing pin 95 removably penetrates the outer sidewall 17 and an inner wall 15 of the housing, to secure the retraction spring 86 in an initial stored position.

Figure 1E:
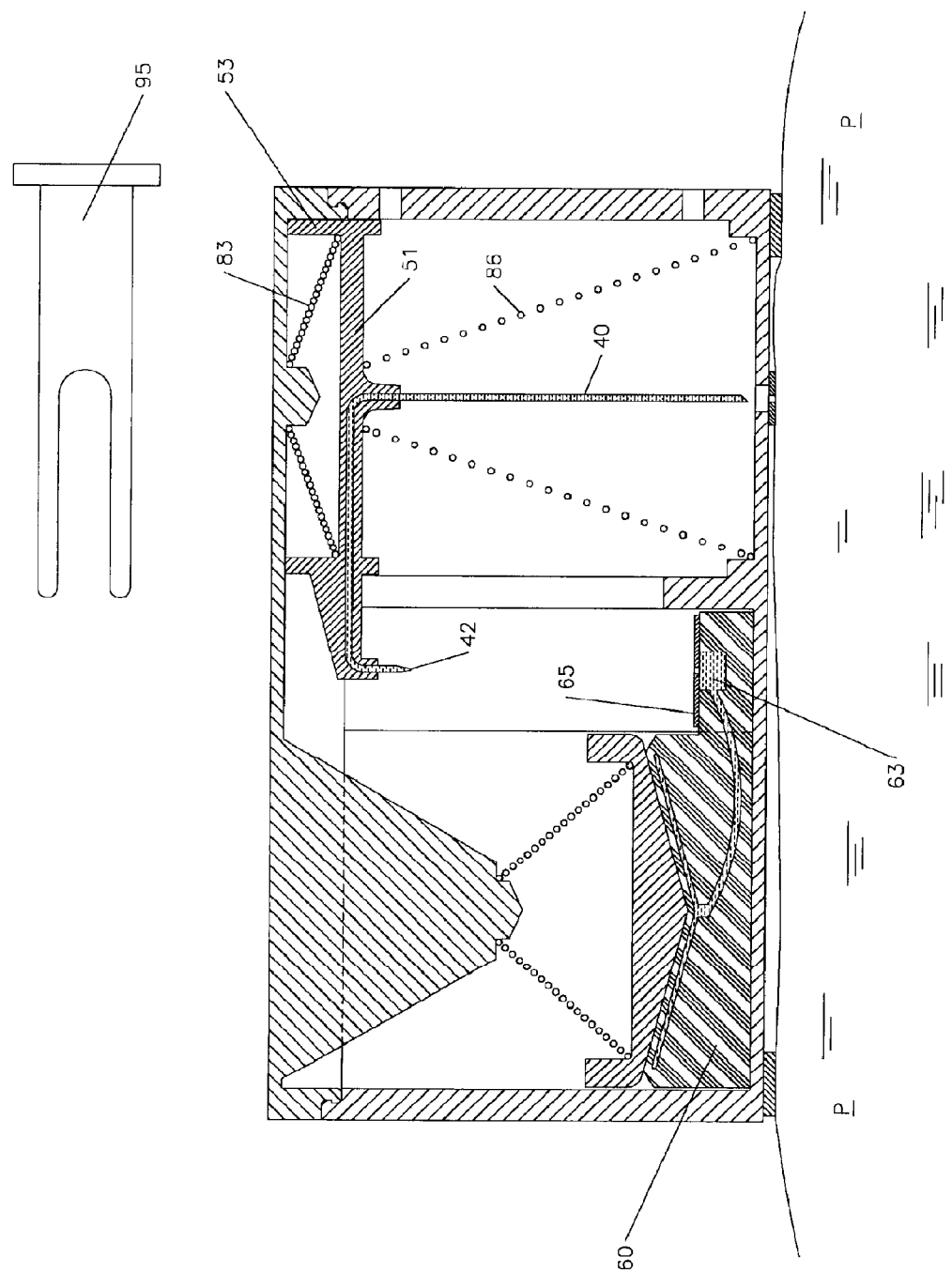
FIG. 1e shows a cross sectional view of the painless injection device of FIG. 1b, showing the retracted needle.

To retract the injection needle 40, the second securing pin 95 is removed, as shown in FIG. 1*e*. The retraction spring 86 then drives the insertion driving plate 51, with the needle 40 secured therein, upward along the axis of the insertion needle until stopped by a retraction stop 53. The retraction spring 86 is configured to have a force greater than the insertion spring 83, and in the illustrated embodiment, a force great enough to cause the insertion driving plate 51 to be displaced to substantially its initial position, and for the tip 41 of the injection needle to be retracted to its third position within the housing. Concurrently, the inlet opening 42 end of the injection needle is extracted from penetrable membrane 65 and the inlet port 63, thereby interrupting fluid communication of the reservoir 60 with the injection needle 40.

The injection needle 40 optionally can be configured in two sections. The first section can be a substantially linear length of needle that is secured to insertion drive plate 51 using conventional means, such as a Liter connection having a simple thread locking mechanism that permits the base of the needle to be screwed onto the hub of the drive plate. Other means can include adhesives, spot welding for permanent or removable attachment of the needle to the insertion drive plate. The second section can be a length of conduit, such as a plastic or non-corrosive metallic tubing, that is shown in-molded- Alternatively, the needle inserting means, pumping means, and needle retracting means can individually or collectively comprise an electro-mechanical system. The device can have a first mechanism comprising an electrical coil around a metal slug which exhibits magnetic activity. The injection needle is affixed within an axial hole in the slug. The needle inserting means can be actuated by activating a switch (such as depressing a button or turning a knob) to send electric current supplied by an on-board battery through the coil. The flow of current through the coil causes the slug with the onboard needle to move axially into the patient to its stopped insertion depth.

A second electrical coil and second slug can provide a medicament pumping means. When actuated with an onboard battery, the second slug, affixed to a plunger, can exert pressure upon a flexible reservoir member, thereby driving liquid medicament to the injection needle. An electrically-actuated valve can be opened in the pathway of liquid communication to allow liquid medicament to flow to the injection needle. The second coil can be activated manually, or automatically by an electrical or mechanical switch in response to the insertion of the injection needle to its full depth of insertion. The force can continue to exert pressure on the flexible medicament reservoir until the medicament therein is depleted.

After the medicament has been depleted, the first coil and slug mechanism can be reversed to retract the needle. The reversal can comprise a revering of the polarity of the electrical current, causing the slug to move in the opposite direction to retract the needle. The reversal can also be accomplished by providing a biasing spring that biases the needle toward the retracted position. The biasing spring can be overwhelmed by the force of the slug during insertion, but when the electrical current to the coil is turned off, the biasing spring can drive the slug and the needle to the retracted position.

In another alternative embodiment, the needle inserting means, pumping means, and needle retracting means can individually or collectively comprise a pneumatic activating means. An embodiment of such a pneumatically driven device is later described in the fourth embodiment.

Figure 3A:
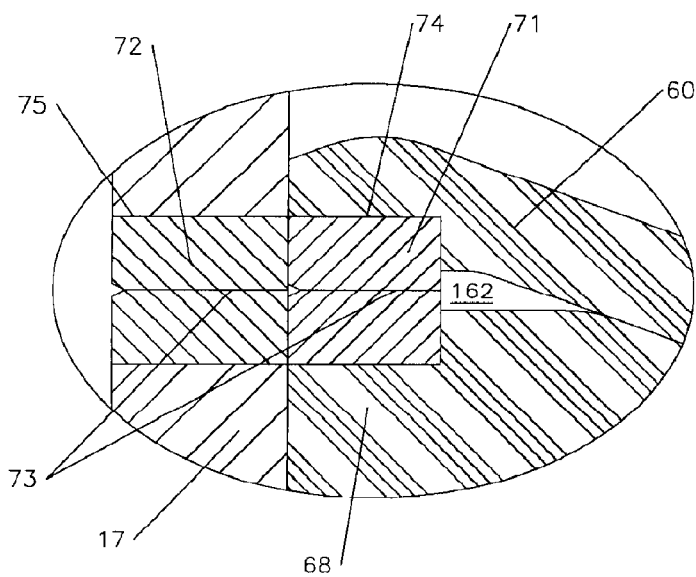
FIG. 3a shows a cross-sectional view of medication flow valve that can providing filling of a reservoir in the device with medication.
Figure 3B:
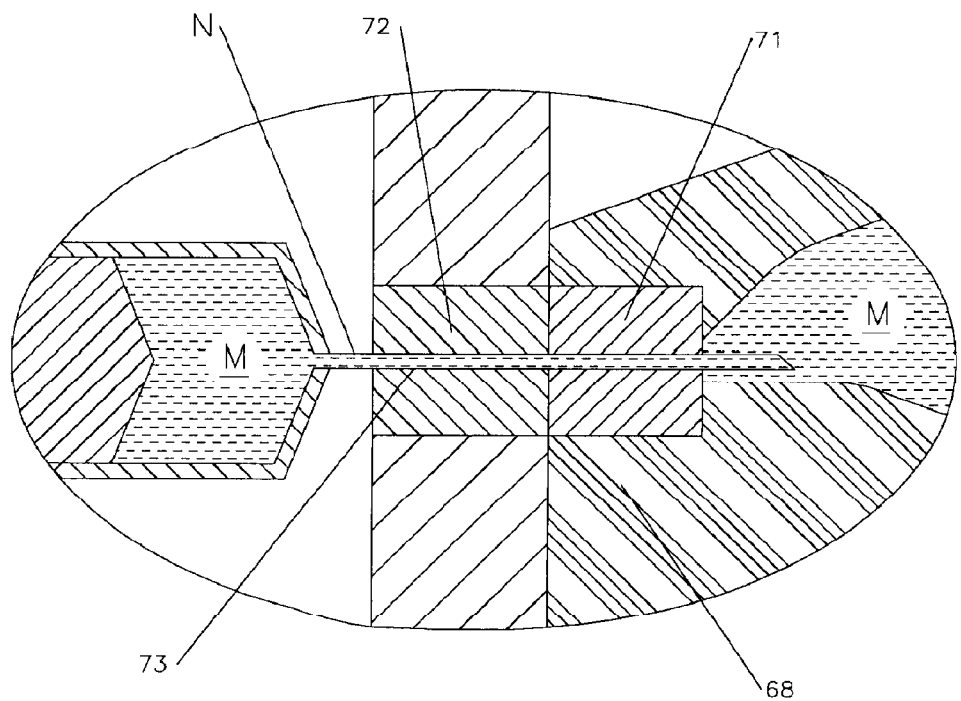
FIG. 3b shows a cross-sectional view of the medication flow valve of FIG. 3a showing a needle injecting medicine into the reservoir.

In an embodiment of the device of the present invention and illustrated in FIGS. 3*a* and 3*b*, a device can comprise a pair of medication flow valves 71 and 72 projecting laterally through the sidewall 17 of the device 1 and the sidewall 68 of the reservoir 60, respectively. The flow valves can be inserted into the sidewall 17 of the housing 10 and the sidewall 68 of a reservoir, such as in the device of FIG. 1*b* (though not shown). The flow valves 71 and 72 each comprise a self-closing, self-sealing passage, shown as a slit opening 73, through which a filling needle N can be inserted to inject medication M into the cavity 162 of the reservoir 60. In a typical embodiment, the medication flow valves 71,72 comprise an elastic, cylindrical core configured with a circumferential size slightly larger than the cylindrical bore 74 in the reservoir sidewall and the bore 75 in the housing sidewall. The bore 74,75 each exert radial compression upon the valves 71,72, which force the inner walls of the respective slit opening 73 tightly together, effecting a seal that prevent leakage of liquid back there through. The filling needle N can be inserted through the slit openings 73 for dispensing the medication M into the reservoir 60.

Using the medication flow valves, a medical personnel can select the type and quantity of medicament to administer, and can inject the dose into the cavity of the reservoir using a conventional hypodermic needle and syringe. The device is then ready for administering to a patient.

In a second embodiment of the present invention, the invention provides a self-contained device for painless, inter-muscular injection of a liquid medicament, comprising a housing, an injection needle, a reservoir containing a liquid medicament, a means for liquid communication between the reservoir and the injection needle, a first means for inserting the injection needle, and a means for pumping the medication from the reservoir to an injection end of the needle.

More specifically, the second embodiment provides self-contained device for painless, inter-muscular injection of a liquid medicament, comprising: a) a housing having a base for attachment to the skin of a patient, b) an injection needle disposed substantially perpendicular to the base and within the housing, the needle having an outside diameter less than about 0.38 mm, an inlet end and an opposed injection end, and configured for axial movement between a first position wherein the injection end is within the housing and a second position wherein the injection end extends outwardly from the base to a distance sufficient for intramuscular insertion thereof, c) a reservoir containing a liquid medicament, disposed within the housing along a line extending axially from the inlet end of the injection needle, d) a means for inserting the injection needle to its second position, and e) a reservoir urging means for moving the reservoir into liquid communication with the inlet end of the injection needle.

An illustration of the second embodiment is shown in FIGS. 2a-2d. The configuration of the second embodiment has similarities to that of the first embodiment. A distinction relates to the positioning of the reservoir 60. The embodiment shows the injection needle 40 having a linear configuration, with a tip 41 and an opposing inlet opening 42. The reservoir 60 is shown in axial alignment with the inlet opening 42 of the needle. This configuration provides a means of fluid communication between the reservoir 60 and the inlet opening 42 that is not completed or established until the two elements move axially into engagement when the injection is administered. The means of fluid communication comprises a penetrable portion sealably covering an outlet 67 of the reservoir 60. The penetrable portion is illustrated as a penetrable membrane 65. The penetrable membrane 65 is positioned along the axis of the injection needle in a position and orientation that faces the inlet opening 42 of the injection needle, and is typically oriented substantially normal to the axis of the needle. Typically the penetrable membrane 65 is adapted to prevent any leakage of the liquid medicament along the outer surface of the inlet opening end, to form a leak-proof or leak-resistant joint between the inlet opening 42 of the injection needle and the reservoir 60. The inlet opening 42 of the needle can also be configured to provide a sealing member 43 positioned along the outer surface of the inlet end of the needle for engaging the penetrable membrane 65.

Figure 2A:
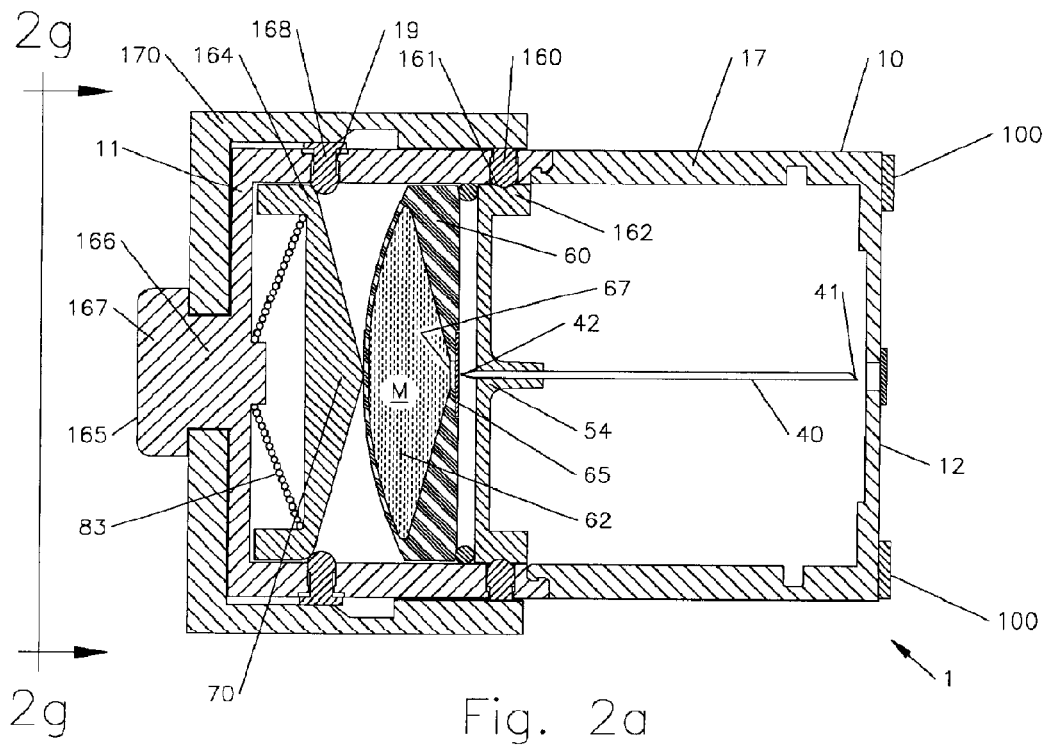
FIG. 2a shows a cross sectional view of another embodiment of a painless injection device of the present invention.

The embodiment illustrated in FIG. 2a shows a device 1 having a substantially circular housing 10 having a base 12, a top 11 and a cylindrical sidewall 17. An injection needle 40 is secured to a forward driving member 54 for axial movement within the housing 10. The forward driving member 54 is initially retained in a stored position shown in FIG. 2a by a plurality of a first securing pin 160 which are biased by an outer cap 170 into restrictive engagement with mating detents 161 in the sidewall 162 of the forward driving member 54.

The reservoir 60 is positioned within the housing and above the forward driving member 54. The reservoir 60 has a cavity 62 filled with a liquid medicament M. In its initial position, the penetrable member 65 lays in proximity but spaced apart from the inlet opening 42 end of the needle 40 by a snap ring 163 that separates the bottom of the reservoir from the upper surface of the forward driving member 54. The bottom of the reservoir 60 is configured to be rigid, whereby the snap ring 163 prevent the inlet opening 42 from penetrating the penetrable member 65. The snap ring is biased radially outwardly, and is held in lateral compression by the inner surface of the sidewall 17.

A drive plunger 70 is positioned above the reservoir 60 and is configured for axial movement within the housing. An insertion or drive spring 83 is shown positioned in compression between plunger 70 and the top portion 11 of the housing. A plurality of a second securing pin 168 is disposed within an opening 19 in the sidewall 17, and is biased inwardly by the outer cap 170 into restrictive engagement with the bottom edges 164 of the plunger 70, to secure the plunger 70 and thereby restrain the drive spring 83 in an initial, compressed stored position.

Figure 2B:
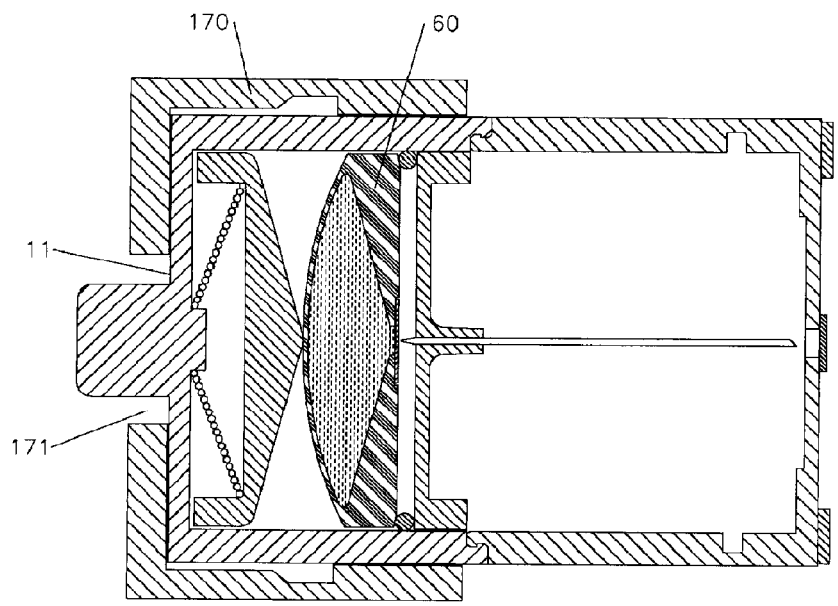
FIG. 2b shows a cross sectional view of the painless injection device of FIG. 2a, taken along section line 2b-2b of FIG. 2g.
Figure 2C:
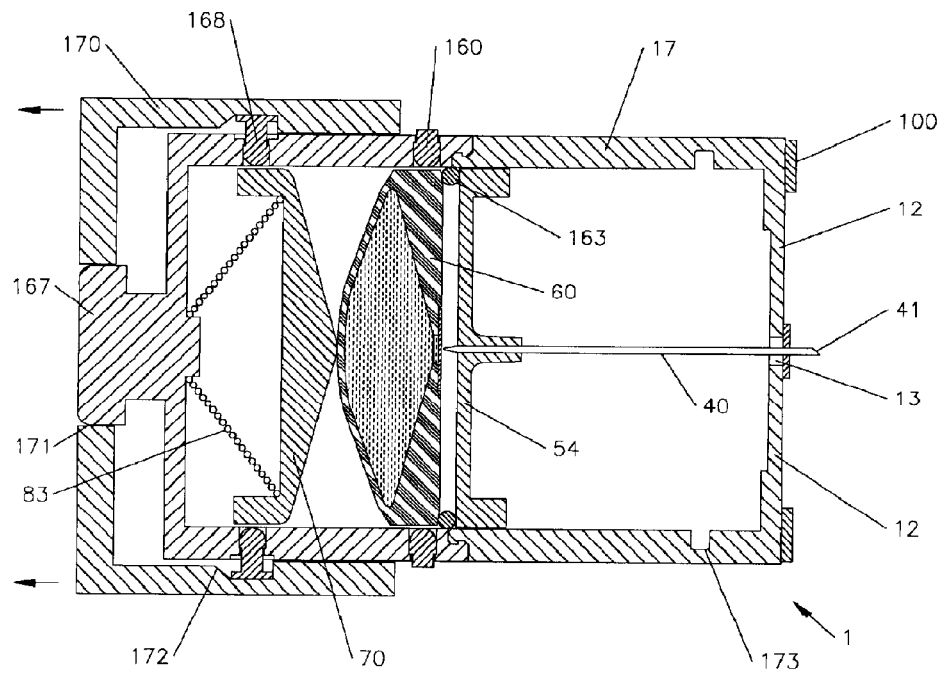
FIG. 2c shows a cross sectional view of the painless injection device of FIG. 2a, showing the device as activated for insertion of the needle.

Integral with the top 11 of the housing is a security pin 165 having a cylindrical stem 166 and an elongated crown 167. The security pin 165 is positioned within an elongated opening 171 formed in the outer cap 170. The elongated opening 171 is configured substantially to accept therein the elongated crown 167. In FIGS. 2a and 2b, the outer cap is illustrated in a stored position, wherein the elongated opening 171 in the cap is oriented perpendicular to the elongated crown 167, as also illustrated in plan view FIG. 2g.

Figure 2D:
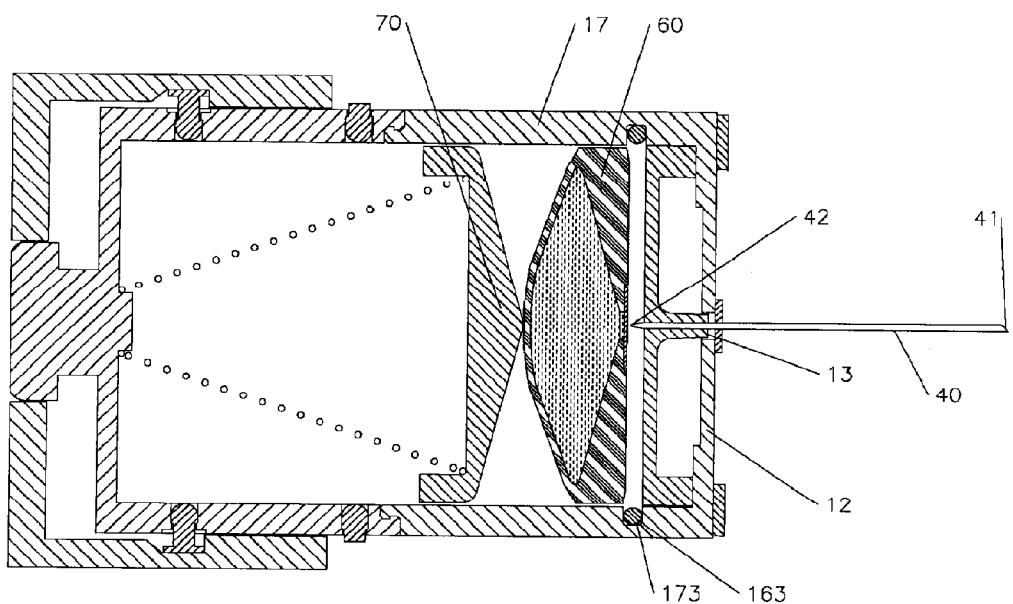
FIG. 2d shows a cross sectional view of the painless injection device of FIG. 2a, showing an inserted needle.

The device 1 is first attached to the skin of a patient by positioning the base 12 against the skin at the injection site. Adhesive portions 100 secure the device to the skin. Once attached, the device is "armed" by rotation of the outer cap 170 by about a quarter turn to a second position, shown in FIG. 2c relative to FIG. 2a, wherein the elongated opening 171 aligns with the elongated crown 167. The device is then activated by moving outer cap 170 axially outward, causing the sidewall of the outer cap 170 to uncover and unrestrain first securing pins 160 and second securing pins 168. The force of restrained drive spring 83 upon the plunger 70 is communicated to the reservoir 60 and the insertion driving plate 54, which force first securing pins 160 out of detents 161 in the inserting driving plate 54, and second securing pins 168 outward to a relief cavity 172 in the inner sidewall of the outer cap 170. The plunger 70 descends through the housing, pushing ahead of it the reservoir and the forward driving member 54, which drives the tip 41 of the injection needle 40 downward through the opening 13 and into the tissue of the patient. When the forward driving member arrives at the base 12, the snap ring 163 expands laterally outwardly into recess 173 in the lower portion of the sidewall 17, as shown in FIG. 2d.

Figure 2E:
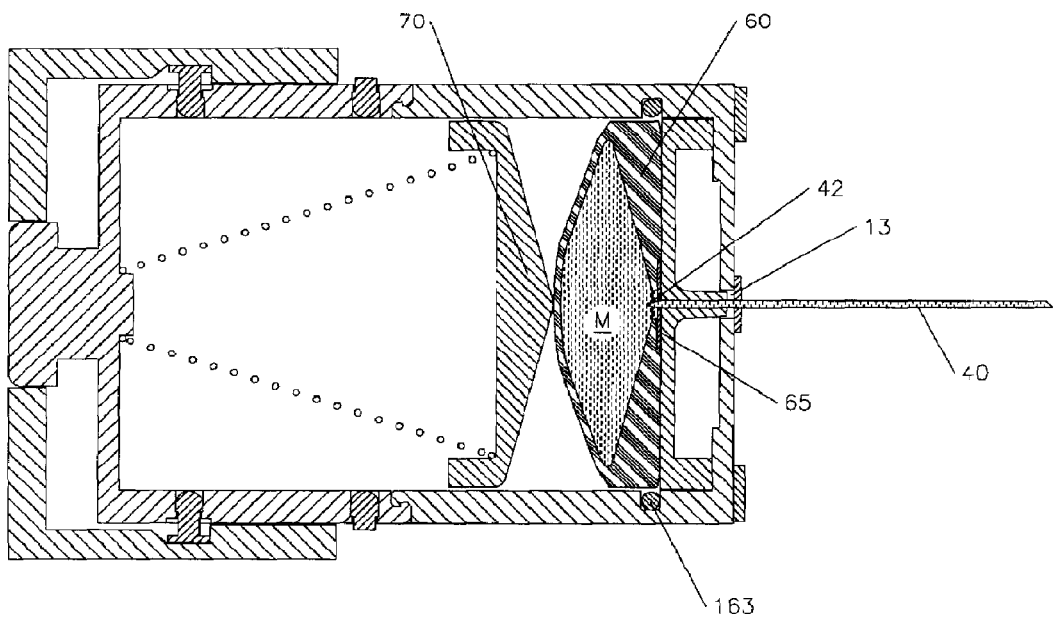
FIG. 2e shows a cross sectional view of the painless injection device of FIG. 2a, showing liquid medicament injection through an inserted needle.
Figure 2F:
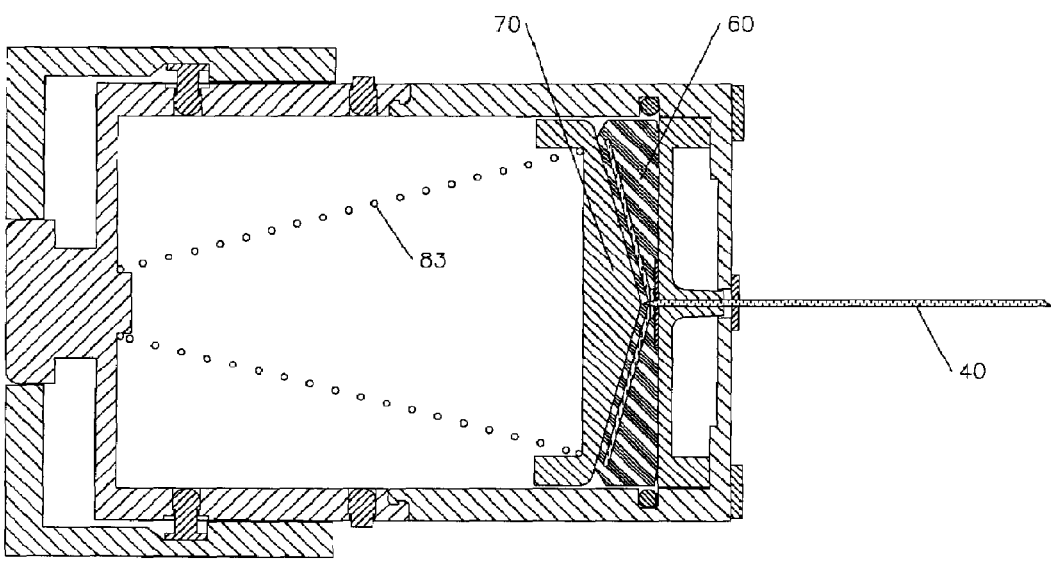
FIG. 2f shows a cross sectional view of the painless injection device of FIG. 2a, showing completion of the liquid medicament injection.
Figure 2G:
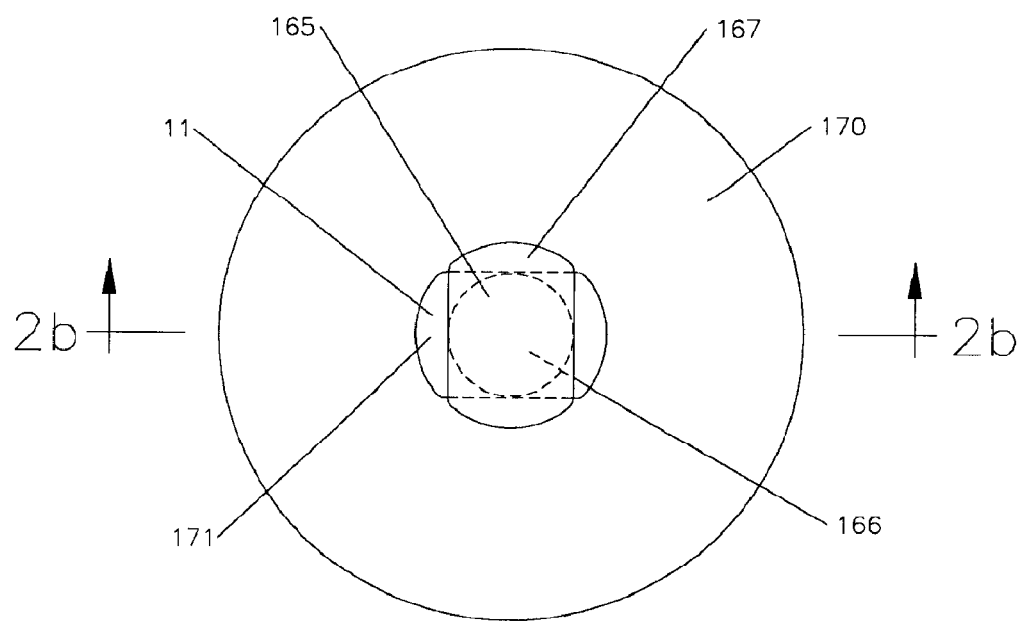

The piston 70 then continues its descent by forcing the reservoir 60 against the inlet opening 42 of the needle, thereby causing the inlet opening 42 to penetrate through the penetrable membrane 65 and placing the needle into liquid communication with the medicament M contained in the reservoir 60, as shown in FIG. 2e.

While the present embodiment comprises a mechanical (spring) urging means for placing the reservoir and injection needle into liquid communication, other means can be effectively used. Alternatively, the force to axially urge the medicament reservoir onto the distal end of the needle, can be provided: by an electro-mechanical means, such as an actuated electrical coil and slug mechanism, affixed to a plunger; by an pneumatic means; by an electro-chemical means, such as a electrolytic gas generator; and mixtures and combinations thereof.

Once placed into liquid communication with the needle 40, the reservoir 60 dispenses its contents under the constant force of the drive spring 83, thereby pumping the liquid medication into the patient's tissue. In the illustrated embodiment, a single drive spring 83 provides the needle inserting means, the reservoir urging means, and the pumping means.

In the illustrated embodiment, the injection needle can be withdrawn from the patient by manual grasping the housing and lifting the device away from the skin.

Figure 5:
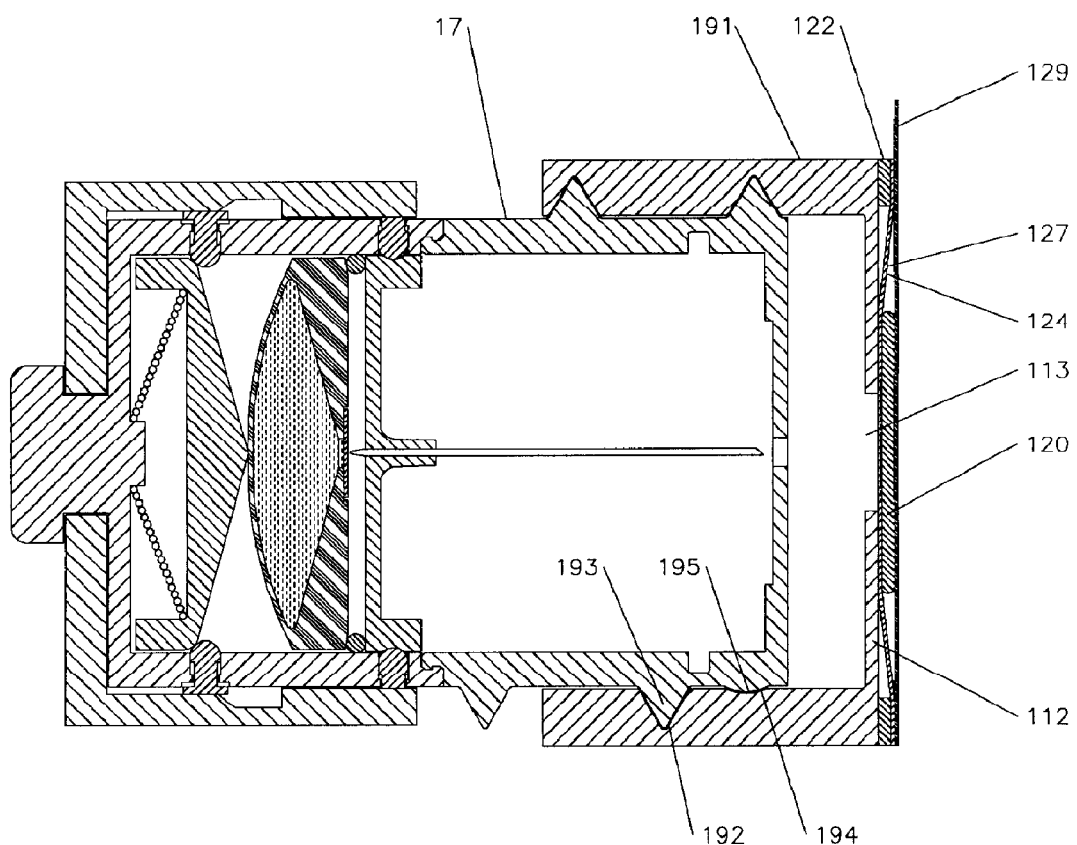
FIG. 5 shows a cross sectional view of another embodiment of the painless injection device, showing a means for preselecting the depth of needle insertion.

In an alternative embodiment of the present invention the device 1 shown in FIG. 5 further comprises a means for pre-selecting the depth of needle insertion. This illustrated embodiment is similar to the one shown in FIG. 2a, and further comprises an adjusting member 191 comprising an adjustable base 112. The adjusting member 191 is configured to be adaptably positioned over the base 12 end of the housing 12. The adjusting member 191 has a spiraling thread groove 192 that is configured to mate with a thread 193 on the base 12 end of the housing sidewall 17. The thread and thread groove are configured to the adjustable base 112 away from of toward the base 12 of the housing when rotated there around. A stub 195 can be disposed along the outer surface of the sidewall of the housing to releasably engage a plurality of detents 194 disposed in the adjusting member 191 to signal incremental adjustments in height as the adjusting member is rotated. In the embodiment, the forward driving plate 54 is stopped on its forward movement by the base 12 of the housing, whereby the variation in the depth of penetration is controlled by the adjustability of the adjusting member 191.

The device is thereby configured to allow a medical technician, nurse, or doctor, or the patient herself, to pre-select the depth at which the tip of the injection needle will extend below the surface of the skin when at its second, inserted position. As earlier described, it is expected that medical technicians and physicians will adequately judge the appropriate depth of insertion of a specific patient, and adjust the device accordingly. The housing or the adjusting member 191 can be provided with markings to indicate the pre-selected depth of insertion, depending upon the rotational position of the adjusting member upon the housing 10.

The pre-selected depth inserting means can be configured as a mechanical means, electro-mechanical means, or other equivalent means. An alternative stopping means can be as basic as the use a pin or peg that can be inserted into one of a series of holes disposed in the sidewall of the housing and extending from the base, thereby creating a stop on the inner surface of the sidewall to impede the passage of the forward driving member The configuration of a means for pre-selecting the depth of needle insertion can also be used on any of the other embodiments of the invention described herein.

In a third embodiment of the present invention, the invention provides a self-contained device for painless, inter-muscular injection of a liquid medicament, comprising a housing, an injection needle, a reservoir containing a liquid medicament, a means for liquid communication between the reservoir and the injection needle, a first means for inserting the injection needle, and a means for pumping the medication from the reservoir to an injection end of the needle at a substantially constant volumetric flow rate.

More specifically, the second embodiment provides a) a housing having a base for attachment to the skin of a patient, b) an injection needle disposed substantially perpendicular to the base and within the housing, the needle having an outside diameter less than about 0.38 mm, inlet end and an opposed injection end, and being configured for axial movement between a first position wherein the injection end is within the housing and a second position wherein the injection end extends outwardly from the base, c) a reservoir containing a liquid medicament, d) a means for liquid communication between the reservoir and the injection needle, e) a means for inserting the injection needle to its second position, f) a means for pumping the medicament from the reservoir to the injection end of the injection needle at a substantially constant volumetric flow rate of from about 0.5 µL/s to about 20 µL/s.

The third embodiment is similar to the previously described first embodiment. A distinction relates to the rate of injection of the liquid medicament from the reservoir, to and through the injection needle, and into the body of the patient. As mentioned hereinabove, a typical intramuscular injection, such as for a vaccine, requires an average volumetric flow rate of at least about 0.05 µL/s, and up to about 50 µL/s. The present embodiment, however, requires that the volumetric rate of pumping to the body be substantially constant in volumetric rate throughout the term of the injection, within a prescribed rate range of about 0.5 µL/s to about 20 µL/s. More preferably, the substantially-constant volumetric flow rate is from about 1 µL/s to about 4 µL/s.

The medicament pumping means can be selected from any pumping system that can provide the required controlled, constant volumetric flow rate of medicament. Typically, the mass density of most medicaments are substantially the same, such that a pumping means system that can deliver a constant volumetric flow rate of medicament will deliver equivalent mass rates for a variety of different medicaments. The other important physical property of the medicaments is its viscosity. A typical pumping means for delivering a constant volumetric flow rate can be configured to maintain a constant rate and volume delivery across the broad range of viscosities.

A medicament pumping means of the invention for delivering a constant volumetric rate can be selected from the group consisting of a mechanical pumping means, a pneumatic pumping means, an electro-mechanical pumping means, and piezo-electric pumping means.

A typical pumping means also can be programmed to deliver the volume of medicament at a pre-selected volumetric flow rate. For this purpose, a pumping means that is powered and controlled electronically is preferred.

A pumping means can comprise a micropump, typically made of plastic, that can mechanically pump liquid at rates of up to 2 ml/min, and are described in "A plastic micropump constructed with conventional techniques and materials", Böhm et al., Sensors and Actuators, 11 (1999), 223-228, incorporated herein by reference.

In a preferred embodiment, the pumping means comprises a pump that is made using MicroElectroMechanical Systems (MEMS) technology. MEMS technology uses procedures similar to those used for building semiconductor electronic devices in silicon containing substrates to form micromechanical systems that may be powered electrically. Although MEMS pumps are often micromachined using these fabrication procedures, the end result is a micromechanical device capable of precisely metering quantities of medicaments by accurately pumping in increments as small as a few nanoliters per second (nl/s). At this writing these MEMS pumps have the capability of pumping at rates of up to a few hundred nanoliters per second. However, the size of these pumps is extremely small, and usually no more than a few millimeters (mm) square with the thickness of a semiconductor wafer. Their manufacture by semiconductor fabrication techniques allows large supply quantities at low cost relative to other pumps. A description of the design, fabrication, and operation of MEMS technology in pumps is described in "A High-Performance Silicon Micropump for Disposable Drug Delivery Systems", Maillefer et al., PUBLISHED 2001, incorporated herein by reference.

A medicament pumping means can comprise a single MEMS pump, or a plurality of MEMS pumps, arranged for series or parallel flow, or both, to supply the needed delivery rate of medicament to the injection needle.

In one specific embodiment, a plurality of MEMS pumps are connected in parallel to provide medicament delivery at a rate of about 2.7 microliter per second (µl/s) against a back-pressure produced by flow of the medicament through a standard hypodermic needle having an outside diameter of greater than about 0.2 mm, and less than about 0.38 mm. Each pump supplies approximately the same volume of medicament. Because of the small size of the pumps and their low profile, highly accurate medicament delivery rates can be reached and maintained, and the pumps can be contained in a stand alone, self-contained device for administering intramuscular injections using the painless device discussed above.

The array of MEMS pumps can be powered by a common power source such as a reciprocally moving plate having a variable frequency of reciprocation suitable to drive the pumps and to tune the output of the pumps to the desired output rate. This common pump excitation mechanism can be varied to control the rate of medicament delivery.

Alternatively, the MEMS pumps can be driven individually using individually activated moving members such as a piezoelectric crystal for excitation of the pumps' pumping mechanism. In this aspect, each pump can be turned on or off individually, and the pumping rate can be changed for each individual pump to accurately deliver at a varying rate.

Various other additional embodiments of the present invention are described, which are similar in configuration, element selection, and function to previously illustrated embodiments.

In a fourth embodiment of the present invention, the invention provides a self-contained, automatically sequencing device for painless, inter-muscular injection of a liquid medicament, comprising a housing, an injection needle, a reservoir containing a liquid medicament, a means for liquid communication between the reservoir and the injection needle, a means for inserting the injection needle, and a means for pumping the medication from the reservoir to an injection end of the needle, a means for retracting the injection needle, and a means for automatically sequencing and activating the inserting means, the pumping means and the retracting means.

More specifically, the seventh embodiment provides a self-contained, automatically-sequencing device for painless, inter-muscular injection of a liquid medicament, comprising: a) a housing having a base for attachment to the skin of a patient, b) an injection needle disposed within the housing, the needle having an outside diameter less than about 0.38 mm, an inlet end and an opposed injection end, and being configured for movement between a first position wherein the injection end is within the housing and a second position wherein the injection end extends the base, c) a reservoir containing a liquid medicament, d) a means for liquid communication between the reservoir and the injection needle, e) a means for inserting the injection needle to its second position, f) a means for pumping the medicament from the reservoir to the injection end of the needle, g) a means for retracting the injection needle from its second position to a third position within the housing, and h) a means for automatically sequencing and activating the inserting means, the pumping means and the retracting means.

Figure 4A:
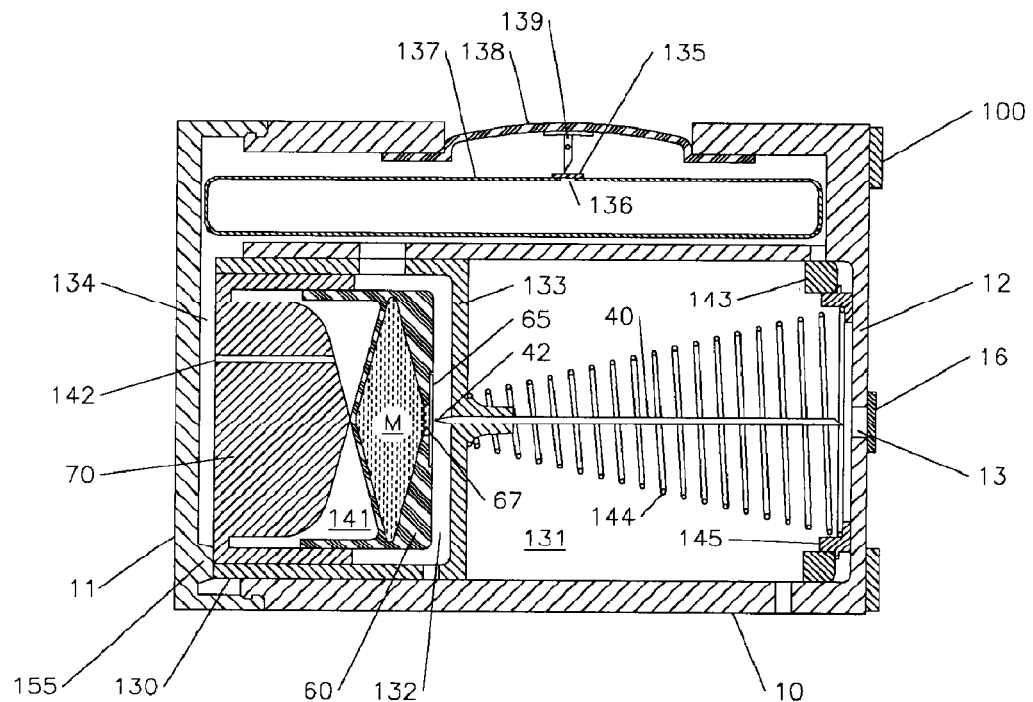
FIG. 4a shows a cross sectional view of another embodiment of a painless injection device of the present invention.
Figure 4B:
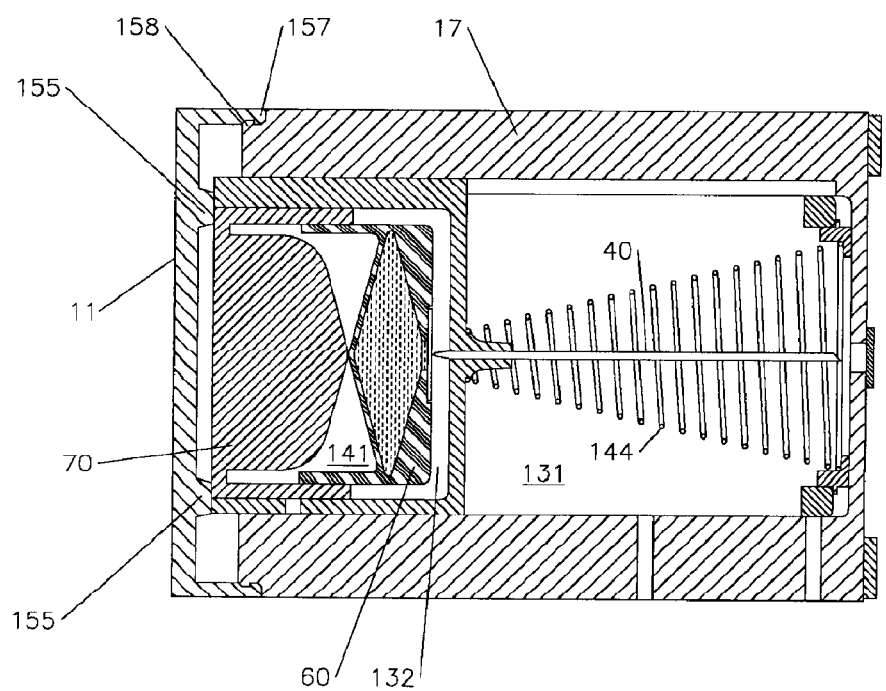

FIGS. 4a-4b show an embodiment of a device that is driven pneumatically by the release of gas from a pressurized gas container 137 onboard the device. An insertion assembly 130 is provided within a cylindrical chamber 131, and comprises a carriage 133, a plunger 70, a reservoir 60, and the injection needle 40. The insertion assembly is initially configured with an internal chamber 132 between the reservoir 70 and the bottom of the carriage 133. The inside of the top 11 of the housing has an offset stub 155 that is positioned to prevent both the carriage 130 and the plunger 70 from resting against the top 11.

The device is initially activated by puncturing a seal 135 that covers an opening 136 in the side of the onboard pressurized gas container 137. The seal 135 is punctured by depressing a portion of the outer surface of the housing illustrated as a button 138, which drives a wedge such as a nail 139 that punctures the seal 135. The gas container 37 releases its pressurized gas contents, which fills a drive chamber 134 above the insertion assembly 130, and the internal chamber 132. A stand-off chamber 141, positioned between the plunger 70 and the reservoir 60, is also pressurized with gas via a port 142 in the plunger passing between the drive chamber 134 and the stand-off chamber 141. The gas pressure within the drive chamber 134 drives the insertion assembly through the cylindrical chamber 131 toward the base 12. During this motion, the gas pressure within the stand-off chamber 141 initially prevents the driven plunger 70 from substantially compressing the reservoir 60, and the gas pressure within the internal chamber 132 prevents a penetrable membrane 65 sealably covering the opening 67 in the bottom of the reservoir 60 from moving against the sharpened inlet opening 42 of the injection needle.

Figure 4C:
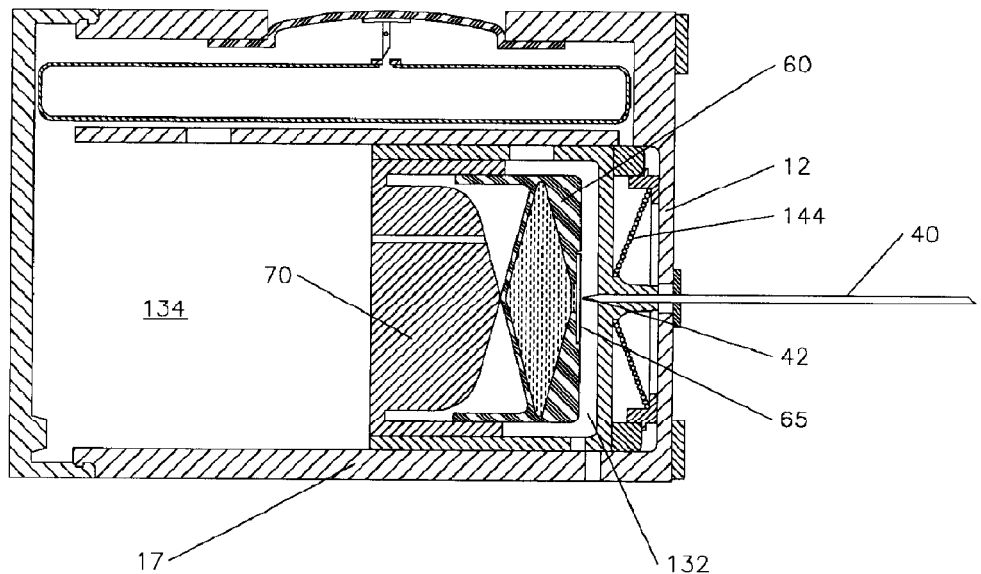
FIG. 4c shows a cross sectional view of the painless injection device of FIG. 4a, showing an inserted needle.

As insertion assembly 130 passes through the cylindrical chamber 131 toward the base 12, a retraction spring 144, shown expanded in FIG. 4a, is forced into and held in compression against the bottom 12 as shown in FIG. 4c. The driven insertion assembly 130 thereby inserts the needle 40 into the tissue of the patient.

Figure 4D:
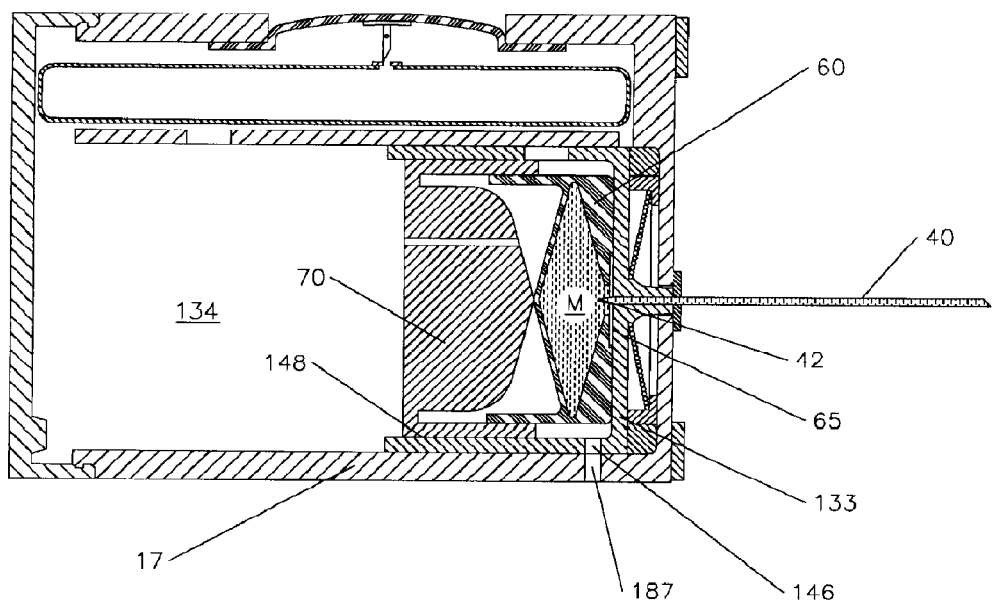
FIG. 4d shows a cross sectional view of the painless injection device of FIG. 4a, showing liquid medicament injection through an inserted needle.

The arrival of the insertion assembly 130 at the base 12 depresses block element 143, allowing the bottom of the carriage 133 to press down onto stop 145. (Block element 143 initially prevented gas from pressurizing cylindrical chamber 131). Simultaneously, as shown in FIG. 4d, a first bleed port 146 in the insertion carriage 133 aligns with a vent port 147 in the sidewall 17 of the housing, thereby venting the gas pressure in the internal chamber 132 to atmosphere. This has also allowed the gas pressure in drive chamber 134 to force plunger 70 downward, thereby forcing reservoir 60 against the inlet opening 42 end of the needle 40. The inlet opening 42 punctures through the penetrable member 65 and passes into the reservoir 60, thereby establishing fluid communication between the medication M in the cavity of the reservoir 60 and the needle 40, and initiating the pumping or injection of medicament into the tissue of the patient.

Figure 4E:
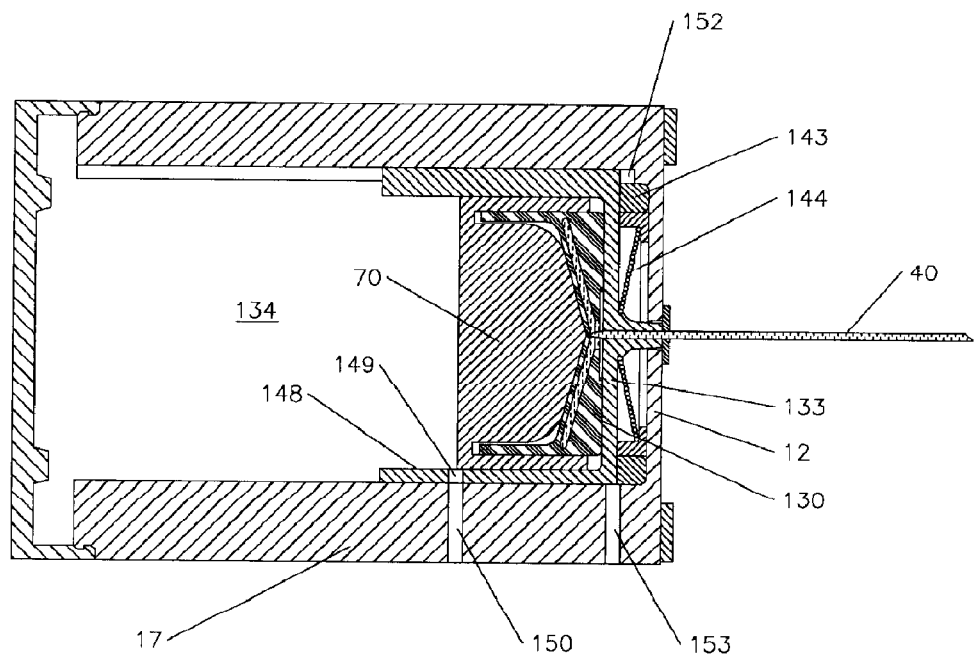
FIG. 4e shows a cross sectional view of the painless injection device of FIG. 4b, showing completion of the liquid medicament injection.
Figure 4F:
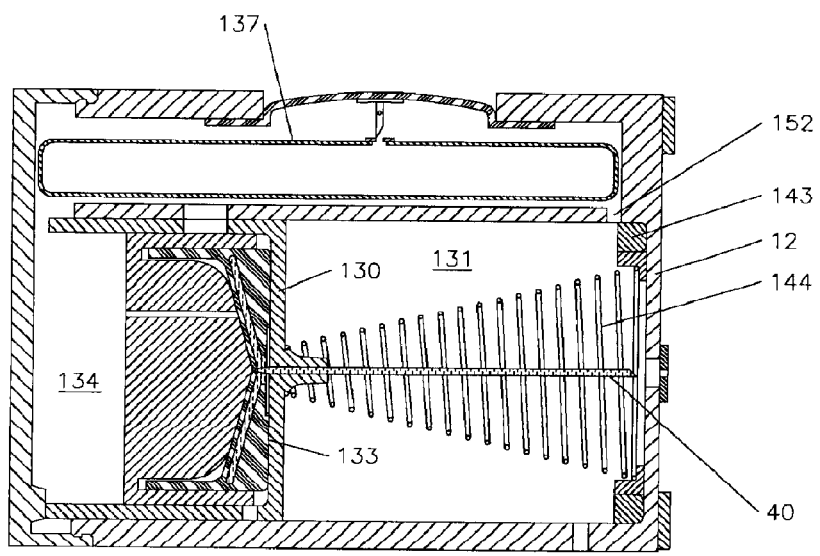
FIG. 4f shows a cross sectional view of the painless injection device of FIG. 4a, showing retraction of the needle.

As the medicament in the reservoir nears depletion, the upper end of the plunger 70 descends along the inner wall 148 of the carriage 133. As shown in FIG. 4e, the inner wall 148 has disposed therethrough a second bleeding port 149. When the carriage 133 is positioned against the base 12, the second bleed port 149 aligns with a second vent 150 in the sidewall 17 of the housing. As the reservoir nears emptiness and the injection procedure nears completion, the descending plunger 70 exposes the second bleed vent 150 to the pressurized gas in drive chamber 134. As gas begins to escape from drive chamber 134 through the second bleed vent 150, the pressure in the drive chamber 134 begins to decrease. At a certain pressure, the force of the retracting spring 144 begins to raise the insertion assembly 130 off of the base 12. As soon as the bottom of carriage 133 raises off of ring element 143, first 152 and second 153 final vent ports become exposed and can vent gas pressure from chambers 134 and 131 to atmosphere, allowing the retraction spring 144 to retract the needle 40 completely from the patient's tissue and into the housing, as shown in FIG. 4f. Since the pressurized gas cylinder 137 has been depleted, the device 1 cannot be reused and the needle 40 is securely biased by the retraction spring 144 to prevent any accidental needle stick.

To assist assembly of the device, the housing can be configured with a sealable top member 11 than can be snapped together to the sidewall of the housing with mating joint elements 157 and 158, as shown in FIG. 4b.

The illustrated embodiment demonstrates one means of providing automatic sequencing and activation of the needle inserting means, the medicament pumping means and the needle retracting means. Additional embodiments employing mechanical, electrical, and electromechanical mechanisms, solely or in combination, are within the ordinary skill of the art in view of the description herein.

In a eighth embodiment of the present invention, the invention provides a self-contained device for injecting a medicament, comprising: a) a housing having a base for attachment to the skin of a patient, b) an injection needle disposed within the housing and having an injection end configured for insertion into the skin of the patient, c) a reservoir containing a liquid medicament and configured for liquid communication with the injection needle, d) a bandage releasable affixed to the base of the housing, comprising a base-contacting surface and a skin-contacting surface that comprises an affixment for attachment of the device to the skin.

More typically, the device and the bandage are configured wherein the attachment of the affixment to the skin is greater than the affixment of the bandage to the base, whereby when the affixed device is removed from the skin, the bandage detaches from the base of the device and remains attached to the skin.

The bandage is configured for releasable securement to the base of the housing. The securement is sufficient to secure the bandage to the base during packaging, shipment, storage, un-packaging, set-up, application of the device onto the skin of the patient, and for the duration of the injection procedure. Once the device has completed the injection of the medication and withdrawn the needle, the device can be released from the bandage and removed from the patient, while the bandage remains secured to the skin of the patient.

Although the injection needle has a very small diameter and its insertion and retraction are essentially painless, the needle does create an opening in the skin tissue. The bandage serves to cover the needle mark in the skin after the injection procedure.

The bandage has a first skin-contacting side and a second device-contacting side. The skin-contacting side comprises an attachment portion which releasably secures the bandage to the skin of the patient. The device-contacting side comprises an attachment portion which releasably secures the bandage to the base of the device.

The skin-contacting side can also comprise a pad portion that can comprises a gauze, wound dressing, or absorbent material that is configured to cover the skin at the wound site. The pad portion typically lies in the interior of the skin-contacting side of the bandage, surrounded by the attachment portion.

The pad can also comprise a second medicament. The second medicament can assist in the healing or protection of the needle mark. The second medicament can be selected from an analgesic, a topical antibiotic, a barrier lotion, or other conventional medicament The securement of the bandage to the device can use various attachment means, including an adhesive attachment and a mechanical attachment. Typically, the bandage is attached to the base of the device with a first adhesive attachment. The first adhesive is selected and applied whereby its adhesion to the device is greater than its adhesion to the attachment portion of the device-contacting side of the bandage. Preferably, the first adhesive is substantially permanently secured to the base of the device. The first adhesive is typically completely released from the attachment portion of the device-contacting side of the bandage. Typically the attachment portion of the device-contacting side of the bandage comprising a releasing surface or a releasing surface treatment, which allows the first adhesive to be temporarily secured thereto, but completely released therefrom when the bandage is separated from the device.

Typically, the bandage is secured to the base of the device whereby any pad portion of the bandage is registered with the opening in the base, whereby the injection needle can penetrate through the pad during insertion to its second positions.

The securement of the bandage to the skin can use various attachment means, although an adhesive attachment is typically advantageous. Typically, the bandage is attached to the skin with a second adhesive attachment. The second adhesive is selected and applied whereby its adhesion to the device-contacting side of the bandage is greater than its adhesion to the skin. Preferably, the second adhesive is substantially permanently secured to the skin-contacting side of the bandage. The second adhesive is typically completely released from the skin, which allows the second adhesive to be temporarily secured thereto, but completely released therefrom when the bandage is later separated from the skin.

The selection of the first and second adhesives provides that the adhesive attachment of the first adhesive to the bandage is less then the adhesive attachment of the second adhesive to the skin. This ensures that when the device is removed from the skin, its will separate from and leave behind the bandage secured to the skin.

The first adhesive and the second adhesive are typically pressure-sensitive adhesives (PSA). Selection of appropriate first and second adhesives is within the ordinary skill of those practicing in the adhesives art.

The second skin-contacting adhesive can also comprise a third medicament. The third medicament can be a complementary medicament to the main injected medicament, or can be selected for an independent indication.

Typically, the illustrated embodiment of the device has a release member, such as a release paper or film, which overlies the second adhesive on its skin-contacting side. The release member is peeled from the second adhesive prior to attachment of the device to the skin.

An embodiment of the invention having a bandage is shown in FIG. 5a. A portion of an adjustable base 112 of the device has first adhesive 122 that releasably secures a bandage 120 to the device. The bandage 120 comprises a planar film 124 and a centrally position pad portion 126 that is disposed over the opening 113 of the adjustable base 112. The planar film 124 has a second adhesive 127 adhered to its skin-contacting surface, for securing the bandage to the skin. A release paper 129 covers adhesive 127 until the device is applied to the skin.

Alternatively, the bandage can be configured and disposed on the base of the device wherein the base adhesive 122 (or adhesive 100 in a device shown in FIG. 2a) secures the device to the skin of the patient, while a bandage 120 can be configured to adhere to the inner portion of the base (inboard of the base adhesive 122) and attaches separately to the skin.

In a fourth embodiment of the present invention, the invention provides a self-contained device for painless, inter-muscular injection of a liquid medicament, comprising: a) a housing having a base for attachment to the skin of a patient, b) an injection needle disposed within the housing, the needle having an outside diameter greater than 0.20 mm and less than about 0.32 mm, having an inlet end and an opposed injection end, and being configured for movement between a first position wherein the injection end is within the housing and a second position wherein the injection end extends through the base, c) a reservoir containing a liquid medicament, d) a means for liquid communication between the reservoir and the injection needle, e) a means for inserting the injection needle to its second position, f) a means for pumping the medicament from the reservoir to the injection end of the injection needle at a substantially constant volumetric flow rate of from about 0.5 µL/s to about 20 µL/s.

In a fifth embodiment of the present invention, the invention provides a) a housing having a base for attachment to the skin of a patient, b) an injection needle disposed substantially perpendicular to the base and within the housing, the needle having an outside diameter less than about 0.038 mm, inlet end and an opposed injection end, and being configured for axial movement between a first position wherein the injection end is within the housing and a second position wherein the injection end extends outwardly from the base, c) a reservoir containing a liquid medicament, d) a means for liquid communication between the reservoir and the injection needle, e) a means for inserting the injection needle to its second position, f) a means for pumping the medicament from the reservoir to the injection end of the injection needle at a substantially constant volumetric flow rate of from about 0.5 µL/s to about 20 µL/s.

In a sixth embodiment of the present invention, the invention provides a self-contained device for painless injection of a liquid medicament, comprising: a) a housing having a base for attachment to the skin of a patient, b) an injection needle disposed substantially perpendicular to the base and within the housing, the needle having an injection end, and configured for axial movement between a first position wherein the injection end is within the housing and a second position wherein the injection end extends outwardly from the base, the injection needle having an outside diameter greater than 0.20 mm and less than about 0.38 mm, c) a reservoir containing a liquid medicament, d) a means for liquid communication between the reservoir and the injection needle, e) a means for pre-selecting the depth of extension of the injection needle at its second position, f) a means for inserting the injection needle to its second position, and g) a means for pumping the medicament from the reservoir to the injection end of the needle.

In a ninth embodiment of the present invention, the invention provides a method of inter-muscular injection painlessly of a liquid medicament, comprising the steps of: a) inserting the injection tip of an injection needle through the skin and into the muscle of a patient, the needle having an outside diameter greater than 0.20 mm and less than about 0.38 mm, and b) injecting the liquid medicament through the needle and into the patient at a substantially constant volumetric flow rate of from about 0.5 µL/s to about 20 µL/s.

In an example of the injection procedure and method, a patient is positioned for attachment of the device to the upper arm for injection into the deltoid muscle. The release paper is removed from the adhesive affixment of the base and the base of the device is adhesively attached to the skin. Once the device is securely affixed to the skin, the device is actuated thereby injecting the injection tip from its first position to its second position, causing the injection tip to pass through the skin and into the muscle. The selected needle between a gauge size lower than 33 gauge and greater than 27 gauge, provide painless injection at an appropriate medication flow rate. Typically, the needle is selected from 28, 29, 30, 31 and 32 gauge.

The device is further actuated to cause a flow of medicament from the reservoir to the injection needle, and through the injection tip and into the patient. Typically, the method provides for injecting the medicament at a substantially constant volumetric flow rate of from about 0.50 µL/s to about 20 µL/s, more typically from about 0.5 µL/s to about 20 µL/s.

In various of the embodiment described herein, a mechanical spring is illustrated as one example of a biasing member or biasing means that can be used to insert the injection needle, pump or dispense the liquid medicament to the needle, and to retract the needle.

In various of the embodiments described herein, the inlet opening end of the injection needle is described as physically restrained from pre-maturely coming into contact with the penetrable membrane positioned over the opening to the reservoir. In some embodiments, it may be possible to prevent relative movement between the forward drive member and the reservoir, for instance, by increasing the coefficient of friction between the outer edges of such members and the inner surface of the sidewall of the housing, thereby preventing accidental piercing prior to needle insertion. Alternatively, the piercing membrane may be configured to provide some additional resistance to perforation, thus requiring a relatively large force for the piercing conduit to pierce the membrane.

In a further embodiment of the invention, any of the described embodiments can also comprise a means of indicating the extent of medicament dispensing from the reservoir. The indication means can comprise a visual means that allows personnel to actually view the remaining contents of the reservoir. An embodiment of a visual indication means can comprise a transparent section positioned in a portion of the housing adjacent the reservoir, to view the reservoir. Further, the reservoir can be provided with a corresponding transparent portion to permit the medical personnel to see the medication contained within the reservoir.

The indication means can also comprise a signal means that signals the end or the approaching end of medicament dispensing. A signal means can comprise a mechanical or electrical switch that is activated by the plunger member as the last remaining contents of the reservoir is dispensed. The signal can be a flag, a pop-out tab, an illuminated light, or any other well known signal.

Another embodiment of the invention can comprise a covering or disguise configured for attachment or placement over the injection device 1 either to provide the device with a pleasurable impression, or to direct the patient's attention away from the device. The covering can be formed as a cartoon character, a zoo animal, or the like. In this way, much of the patient's fear that might be caused by the sight of the device can be alleviated.

In another embodiment of the invention, the housing of the device can be colored coded or have a colored indicator or marking that identifies the particular type or quantity of medication contained within the reservoir. For example, for one certain medication the outer casing 102 may be blue in color. The device can also display various warnings, such as a precaution to avoid needle stick and possible side effects to the medication.

While specific embodiments of the apparatus and method of the present invention have been described, it will be apparent to those skilled in the metalworking arts that various modifications thereto can be made without departing from the spirit and scope of the present invention as defined in the appended claims.

I claim:

1. A self-contained device for injecting a medicament, comprising:
   a) a housing that includes a base,
   b) an injection needle disposed within the housing and having an injection end configured for insertion into the skin of a patient, c) a reservoir containing a liquid medicament and configured for liquid communication with the injection needle, d) a means for injecting the medicament from the reservoir to the injection end of the needle at a substantially constant volumetric flow rate of about 0.05 µL/s to about 50 µL/s, and e) a bandage comprising a base-contacting surface releasably affixed to the base of the housing for semi-permanent attachment of the bandage to the base of the device, and a skin-contacting surface that comprises an affixment for temporary securement of the bandage to the skin.

2. The device according to claim 1 wherein the affixment of the bandage to the skin is greater than the affixment of the bandage to the base, whereby when the attached device is removed from the skin, the bandage detaches from the base of the device and remains attached to the skin.

3. The device according to claim 2 wherein the bandage comprises a pad portion through which the injection needle penetrates when moving between its first and second positions.

4. The device according to claim 3 wherein the pad portion is selected from the group consisting of a gauze, a wound dressing, and an absorbent material.

5. The device according to claim 4 wherein the affixment of the bandage to the skin comprises an attachment portion that includes a second adhesive, wherein the attachment portion surrounds the pad.

6. The device according to claim 2 wherein the affixment of the bandage to the base of the device comprises a first adhesive on the base of the device, and the affixment of the bandage to the skin comprises a second adhesive of the skin-contacting surface of the bandage.

7. The device according to claim 2 wherein the second affixment attaches the device to the skin without requiring medical personnel to hold the device.

8. The device according to claim 2 wherein the affixment of the bandage to the base comprises a first adhesive on the base of the device having an adhesion to the base that is greater than its adhesion to the attachment portion of the device-contacting side of the bandage.

9. The device according to claim 1 further comprising a means for inserting an injection end of the injection needle between a first position wherein injection end is within the housing and a second position wherein the injection end extends outwardly from the base and is inserted into the skin of the patient.

10. The device according to claim 9 further comprising a means for preselecting the depth of extension of the injection end of the needle at its second position.

11. The device according to claim 9 further comprising a means for retracting the injection end of the injection needle from the second position and a third position within the housing.

12. The device according to claim 1 wherein the substantially constant volumetric flow rate is about 0.5 µL/s to about 20 µL/s.

13. The device according to claim 12 wherein the substantially constant volumetric flow rate is about 1 µL/s to about 4 µL/s.

14. The device according to claim 1 wherein the needle has an outside diameter greater than 0.20 mm and less than about 0.38 mm.

15. The device according to claim 14 wherein the needle is selected from the group consisting of a 28 gauge needle, a 30 gauge needle, and a 32 gauge needle.

* * * * *